(12) United States Patent
Keenan et al.

(10) Patent No.: US 11,964,119 B2
(45) Date of Patent: Apr. 23, 2024

(54) SHEATH ASSEMBLY FOR CATHETER PUMP

(71) Applicant: TC1 LLC, St. Paul, MN (US)

(72) Inventors: Richard L. Keenan, Livermore, CA (US); Keif M. Fitzgerald, San Jose, CA (US); Veronica J. Neiman, Union City, CA (US); Phyllis Yuen, Fremont, CA (US)

(73) Assignee: TC1 LLC, St. Paul, MN (US)

( * ) Notice: Subject to any disclaimer, the term of this patent is extended or adjusted under 35 U.S.C. 154(b) by 365 days.

(21) Appl. No.: 17/178,923

(22) Filed: Feb. 18, 2021

(65) Prior Publication Data
US 2021/0187272 A1 Jun. 24, 2021

Related U.S. Application Data

(63) Continuation of application No. 15/812,471, filed on Nov. 14, 2017, now Pat. No. 11,077,294, which is a (Continued)

(51) Int. Cl.
*A61M 25/06* (2006.01)
*A61M 25/00* (2006.01)
(Continued)

(52) U.S. Cl.
CPC ........ *A61M 25/0662* (2013.01); *A61M 60/13* (2021.01); *A61M 60/216* (2021.01);
(Continued)

(58) Field of Classification Search
CPC ...................... A61M 25/0053; A61M 25/0054
See application file for complete search history.

(56) References Cited

U.S. PATENT DOCUMENTS

| 4,964,864 A | 10/1990 | Summers et al. |
| 4,969,865 A | 11/1990 | Hwang et al. |

(Continued)

FOREIGN PATENT DOCUMENTS

| CA | 2256427 A1 | 10/1998 |
| CA | 2322012 A1 | 9/1999 |

(Continued)

OTHER PUBLICATIONS

Convert Megapascal to Psi. https://www.unitconverters.net/pressure/megapascal-to-psi.htm. Accessed Thu Apr. 13, 2023. (Year: 2023).*

(Continued)

*Primary Examiner* — Adam Marcetich
(74) *Attorney, Agent, or Firm* — Armstrong Teasdale LLP

(57) ABSTRACT

A catheter pump includes a catheter body having at least one lumen therethrough, and comprising a distal end and a proximal end. An expandable impeller assembly includes an expandable impeller and an expandable cannula coupled to the distal end of the catheter body and housing the expandable impeller, the expandable cannula comprising a substantially straight segment having a distal inlet and a proximal outlet, the substantially straight segment configured to straddle an aortic valve. The catheter body comprises a proximal vessel contact zone and a distal vessel contact zone that are each proximal to the substantially straight segment, the proximal vessel contact zone and distal vessel contact zone configured to provide a force against an aortic arch to stabilize the expandable impeller assembly across the aortic valve.

20 Claims, 24 Drawing Sheets

Related U.S. Application Data continuation-in-part of application No. 13/801,833, filed on Mar. 13, 2013, now Pat. No. 9,872,947.

(60) Provisional application No. 62/421,930, filed on Nov. 14, 2016.

(51) Int. Cl.
    *A61M 25/01*     (2006.01)
    *A61M 60/13*     (2021.01)
    *A61M 60/216*     (2021.01)
    *A61M 60/411*     (2021.01)
    *A61M 60/824*     (2021.01)
    *A61M 60/867*     (2021.01)
    *A61M 25/09*     (2006.01)
    *A61M 39/06*     (2006.01)
    *A61M 60/148*     (2021.01)
    *A61M 60/414*     (2021.01)
    *A61M 60/422*     (2021.01)
    *A61M 60/818*     (2021.01)
    *A61M 60/829*     (2021.01)

(52) U.S. Cl.
    CPC ........ *A61M 60/411* (2021.01); *A61M 60/824* (2021.01); *A61M 60/867* (2021.01); *A61M 25/0068* (2013.01); *A61M 25/0097* (2013.01); *A61M 25/0108* (2013.01); *A61M 25/0113* (2013.01); *A61M 25/09041* (2013.01); *A61M 39/06* (2013.01); *A61M 60/148* (2021.01); *A61M 60/414* (2021.01); *A61M 60/422* (2021.01); *A61M 60/818* (2021.01); *A61M 60/829* (2021.01)

(56) References Cited

U.S. PATENT DOCUMENTS

| | | | |
|---|---|---|---|
| 4,976,270 | A | 12/1990 | Parl et al. |
| 4,985,014 | A | 1/1991 | Orejola |
| 4,994,017 | A | 2/1991 | Yozu |
| 4,995,857 | A | 2/1991 | Arnold |
| 5,000,177 | A | 3/1991 | Hoffmann et al. |
| 5,021,048 | A | 6/1991 | Buckholtz |
| 5,045,072 | A | 9/1991 | Castillo et al. |
| 5,049,134 | A | 9/1991 | Golding et al. |
| 5,061,256 | A | 10/1991 | Wampler |
| 5,089,016 | A | 2/1992 | Millner et al. |
| 5,092,844 | A | 3/1992 | Schwartz et al. |
| 5,098,256 | A | 3/1992 | Smith |
| 5,106,368 | A | 4/1992 | Uldall et al. |
| 5,112,200 | A | 5/1992 | Isaacson et al. |
| 5,112,292 | A | 5/1992 | Hwang et al. |
| 5,112,349 | A | 5/1992 | Summers et al. |
| 5,129,883 | A | 7/1992 | Black |
| 5,142,155 | A | 8/1992 | Mauze et al. |
| 5,147,186 | A | 9/1992 | Buckholtz |
| 5,163,910 | A | 11/1992 | Schwartz et al. |
| 5,169,378 | A | 12/1992 | Figuera |
| 5,171,212 | A | 12/1992 | Buck et al. |
| 5,190,528 | A | 3/1993 | Fonger et al. |
| 5,195,960 | A | 3/1993 | Hossain et al. |
| 5,201,679 | A | 4/1993 | Velte, Jr. et al. |
| 5,211,546 | A | 5/1993 | Isaacson et al. |
| 5,221,270 | A | 6/1993 | Parker |
| 5,234,407 | A | 8/1993 | Teirstein et al. |
| 5,234,416 | A | 8/1993 | Macaulay et al. |
| 5,290,227 | A | 3/1994 | Pasque |
| 5,300,112 | A | 4/1994 | Barr |
| 5,306,262 | A * | 4/1994 | Weldon ............. A61M 25/0041 604/523 |
| 5,312,341 | A | 5/1994 | Turi |
| 5,344,443 | A | 9/1994 | Palma et al. |
| 5,346,458 | A | 9/1994 | Affeld |
| 5,360,317 | A | 11/1994 | Clausen et al. |
| 5,376,114 | A | 12/1994 | Jarvik |
| 5,393,197 | A | 2/1995 | Lemont et al. |
| 5,393,207 | A | 2/1995 | Maher et al. |
| 5,405,341 | A | 4/1995 | Martin |
| 5,405,383 | A | 4/1995 | Barr |
| 5,415,633 | A * | 5/1995 | Lazarus ............. A61M 25/0158 604/95.05 |
| 5,415,637 | A | 5/1995 | Khosravi |
| 5,437,541 | A | 8/1995 | Vainrub |
| 5,449,342 | A | 9/1995 | Hirose et al. |
| 5,458,459 | A | 10/1995 | Hubbard et al. |
| 5,490,763 | A | 2/1996 | Abrams et al. |
| 5,505,701 | A | 4/1996 | Anaya Fernandez de Lomana |
| 5,527,159 | A | 6/1996 | Bozeman, Jr. et al. |
| 5,533,957 | A | 7/1996 | Aldea |
| 5,534,287 | A | 7/1996 | Lukic |
| 5,554,114 | A | 9/1996 | Wallace et al. |
| 5,588,812 | A | 12/1996 | Taylor et al. |
| 5,609,574 | A | 3/1997 | Kaplan et al. |
| 5,613,935 | A | 3/1997 | Jarvik |
| 5,643,226 | A | 7/1997 | Cosgrove et al. |
| 5,678,306 | A | 10/1997 | Bozeman, Jr. et al. |
| 5,692,882 | A | 12/1997 | Bozeman, Jr. et al. |
| 5,702,418 | A | 12/1997 | Ravenscroft |
| 5,704,926 | A | 1/1998 | Sutton |
| 5,707,218 | A | 1/1998 | Maher et al. |
| 5,722,930 | A | 3/1998 | Larson, Jr. et al. |
| 5,725,513 | A | 3/1998 | Ju et al. |
| 5,725,570 | A | 3/1998 | Heath |
| 5,730,628 | A | 3/1998 | Hawkins |
| 5,735,897 | A | 4/1998 | Buirge |
| 5,738,649 | A | 4/1998 | Macoviak |
| 5,741,234 | A | 4/1998 | Aboul-Hosn |
| 5,741,429 | A | 4/1998 | Donadio, III et al. |
| 5,746,709 | A | 5/1998 | Rom et al. |
| 5,749,855 | A | 5/1998 | Reitan |
| 5,755,784 | A | 5/1998 | Jarvik |
| 5,766,151 | A * | 6/1998 | Valley ............... A61M 39/0247 604/103.07 |
| 5,776,111 | A | 7/1998 | Tesio |
| 5,776,161 | A | 7/1998 | Globerman |
| 5,776,190 | A | 7/1998 | Jarvik |
| 5,779,721 | A | 7/1998 | Nash |
| 5,807,311 | A | 9/1998 | Palestrant |
| 5,814,011 | A | 9/1998 | Corace |
| 5,824,070 | A | 10/1998 | Jarvik |
| 5,851,174 | A | 12/1998 | Jarvik et al. |
| 5,859,482 | A | 1/1999 | Crowell et al. |
| 5,868,702 | A | 2/1999 | Stevens et al. |
| 5,868,703 | A | 2/1999 | Bertolero et al. |
| 5,888,241 | A | 3/1999 | Jarvik |
| 5,888,242 | A | 3/1999 | Antaki et al. |
| 5,897,557 | A | 4/1999 | Kronzer |
| 5,911,685 | A | 6/1999 | Siess et al. |
| 5,921,913 | A | 7/1999 | Siess |
| 5,941,813 | A | 8/1999 | Sievers et al. |
| 5,951,263 | A | 9/1999 | Taylor et al. |
| 5,957,941 | A | 9/1999 | Ream |
| 5,964,694 | A | 10/1999 | Siess et al. |
| 5,971,974 | A * | 10/1999 | Keisz ................ A61M 25/0041 604/523 |
| 6,007,478 | A * | 12/1999 | Siess ................. A61M 25/0053 600/585 |
| 6,007,479 | A | 12/1999 | Rottenberg et al. |
| 6,015,272 | A | 1/2000 | Antaki et al. |
| 6,015,434 | A | 1/2000 | Yamane |
| 6,018,208 | A | 1/2000 | Maher et al. |
| 6,027,863 | A | 2/2000 | Donadio, III |
| 6,053,705 | A | 4/2000 | Schoeb et al. |
| 6,056,719 | A | 5/2000 | Mickley |
| 6,058,593 | A | 5/2000 | Siess |
| 6,068,610 | A | 5/2000 | Ellis et al. |
| 6,071,093 | A | 6/2000 | Hart |
| 6,083,260 | A | 7/2000 | Aboul-Hosn |
| 6,086,527 | A | 7/2000 | Talpade |
| 6,086,570 | A | 7/2000 | Aboul-Hosn et al. |
| 6,106,494 | A | 8/2000 | Saravia et al. |
| 6,113,536 | A | 9/2000 | Aboul-Hosn et al. |

(56) References Cited

U.S. PATENT DOCUMENTS

| | | | |
|---|---|---|---|
| 6,123,659 A | 9/2000 | le Blanc et al. | |
| 6,123,725 A | 9/2000 | Aboul-Hosn | |
| 6,132,363 A | 10/2000 | Freed et al. | |
| 6,132,417 A * | 10/2000 | Kiesz | A61M 25/0041 604/523 |
| 6,135,943 A | 10/2000 | Yu et al. | |
| 6,139,487 A | 10/2000 | Siess | |
| 6,152,704 A | 11/2000 | Aboul-Hosn et al. | |
| 6,162,194 A | 12/2000 | Shipp | |
| 6,176,822 B1 | 1/2001 | Nix et al. | |
| 6,176,848 B1 | 1/2001 | Rau et al. | |
| 6,186,665 B1 | 2/2001 | Maher et al. | |
| 6,190,304 B1 | 2/2001 | Downey et al. | |
| 6,190,357 B1 | 2/2001 | Ferrari et al. | |
| 6,200,260 B1 | 3/2001 | Bolling | |
| 6,210,133 B1 | 4/2001 | Aboul-Hosn et al. | |
| 6,210,318 B1 | 4/2001 | Lederman | |
| 6,210,397 B1 | 4/2001 | Aboul-Hosn et al. | |
| 6,227,797 B1 | 5/2001 | Watterson et al. | |
| 6,228,063 B1 | 5/2001 | Aboul-Hosn | |
| 6,234,960 B1 | 5/2001 | Aboul-Hosn et al. | |
| 6,234,995 B1 | 5/2001 | Peacock, III | |
| 6,245,007 B1 | 6/2001 | Bedingham et al. | |
| 6,245,026 B1 | 6/2001 | Campbell et al. | |
| 6,247,892 B1 | 6/2001 | Kazatchkov et al. | |
| 6,248,091 B1 | 6/2001 | Voelker | |
| 6,254,359 B1 | 7/2001 | Aber | |
| 6,254,564 B1 | 7/2001 | Wilk et al. | |
| 6,287,319 B1 | 9/2001 | Aboul-Hosn et al. | |
| 6,287,336 B1 | 9/2001 | Globerman et al. | |
| 6,295,877 B1 | 10/2001 | Aboul-Hosn et al. | |
| 6,305,962 B1 | 10/2001 | Maher et al. | |
| 6,387,037 B1 | 5/2002 | Bolling et al. | |
| 6,395,026 B1 | 5/2002 | Aboul-Hosn et al. | |
| 6,413,222 B1 | 7/2002 | Pantages et al. | |
| 6,422,990 B1 | 7/2002 | Prem | |
| 6,425,007 B1 | 7/2002 | Messinger | |
| 6,428,464 B1 | 8/2002 | Bolling | |
| 6,447,441 B1 | 9/2002 | Yu et al. | |
| 6,454,775 B1 | 9/2002 | Demarais et al. | |
| 6,468,298 B1 | 10/2002 | Pelton | |
| 6,475,195 B1 * | 11/2002 | Voda | A61M 25/0041 604/523 |
| 6,503,224 B1 | 1/2003 | Forman et al. | |
| 6,508,777 B1 | 1/2003 | Macoviak et al. | |
| 6,508,787 B2 | 1/2003 | Reimund et al. | |
| 6,517,315 B2 | 2/2003 | Belady | |
| 6,517,528 B1 | 2/2003 | Pantages et al. | |
| 6,527,699 B1 | 3/2003 | Goldowsky | |
| 6,532,964 B2 | 3/2003 | Aboul-Hosn et al. | |
| 6,533,716 B1 | 3/2003 | Schmitz-Rode et al. | |
| 6,544,216 B1 | 4/2003 | Sammler et al. | |
| 6,547,519 B2 | 4/2003 | Deblanc et al. | |
| 6,565,598 B1 | 5/2003 | Lootz | |
| 6,609,883 B2 | 8/2003 | Woodard et al. | |
| 6,610,004 B2 | 8/2003 | Viole et al. | |
| 6,613,008 B2 | 9/2003 | Aboul-Hosn et al. | |
| 6,616,323 B2 | 9/2003 | McGill | |
| 6,623,420 B2 | 9/2003 | Reich et al. | |
| 6,623,475 B1 | 9/2003 | Siess | |
| 6,641,093 B2 | 11/2003 | Coudrais | |
| 6,641,558 B1 | 11/2003 | Aboul-Hosn et al. | |
| 6,645,241 B1 | 11/2003 | Strecker | |
| 6,652,548 B2 | 11/2003 | Evans et al. | |
| 6,660,014 B2 | 12/2003 | Demarais et al. | |
| 6,673,105 B1 | 1/2004 | Chen | |
| 6,692,318 B2 | 2/2004 | McBride | |
| 6,709,418 B1 | 3/2004 | Aboul-Hosn et al. | |
| 6,716,189 B1 | 4/2004 | Jarvik et al. | |
| 6,749,598 B1 | 6/2004 | Keren et al. | |
| 6,776,578 B2 | 8/2004 | Belady | |
| 6,776,794 B1 | 8/2004 | Hong et al. | |
| 6,783,328 B2 | 8/2004 | Lucke et al. | |
| 6,790,171 B1 | 9/2004 | Frederik et al. | |
| 6,794,784 B2 | 9/2004 | Takahashi et al. | |
| 6,794,789 B2 | 9/2004 | Siess et al. | |
| 6,814,713 B2 | 11/2004 | Aboul-Hosn et al. | |
| 6,817,836 B2 | 11/2004 | Nose et al. | |
| 6,818,001 B2 | 11/2004 | Wulfman et al. | |
| 6,860,713 B2 | 3/2005 | Hoover | |
| 6,866,625 B1 | 3/2005 | Ayre et al. | |
| 6,866,805 B2 | 3/2005 | Hong et al. | |
| 6,887,215 B2 | 5/2005 | McWeeney | |
| 6,889,082 B2 | 5/2005 | Bolling et al. | |
| 6,926,662 B1 | 8/2005 | Aboul-Hosn et al. | |
| 6,935,344 B1 | 8/2005 | Aboul-Hosn et al. | |
| 6,942,611 B2 | 9/2005 | Siess | |
| 6,949,066 B2 | 9/2005 | Bearnson et al. | |
| 6,966,748 B2 | 11/2005 | Woodard et al. | |
| 6,972,956 B2 | 12/2005 | Franz et al. | |
| 6,974,436 B1 | 12/2005 | Aboul-Hosn et al. | |
| 6,981,942 B2 | 1/2006 | Khaw et al. | |
| 6,984,392 B2 | 1/2006 | Bechert et al. | |
| 7,010,954 B2 | 3/2006 | Siess et al. | |
| 7,011,620 B1 | 3/2006 | Siess | |
| 7,014,417 B2 | 3/2006 | Salomon | |
| 7,022,100 B1 | 4/2006 | Aboul-Hosn et al. | |
| 7,027,875 B2 | 4/2006 | Siess et al. | |
| 7,037,069 B2 | 5/2006 | Arnold et al. | |
| 7,070,555 B2 | 7/2006 | Siess | |
| 7,122,019 B1 | 10/2006 | Kesten et al. | |
| 7,125,376 B2 | 10/2006 | Viole et al. | |
| 7,144,365 B2 | 12/2006 | Bolling et al. | |
| 7,150,711 B2 | 12/2006 | Peter et al. | |
| 7,160,243 B2 | 1/2007 | Medvedev | |
| 7,172,551 B2 | 2/2007 | Leasure | |
| 7,175,588 B2 | 2/2007 | Morello | |
| 7,229,258 B2 | 6/2007 | Wood et al. | |
| 7,241,257 B1 | 7/2007 | Ainsworth et al. | |
| 7,262,531 B2 | 8/2007 | Li et al. | |
| 7,264,606 B2 | 9/2007 | Jarvik et al. | |
| 7,267,667 B2 | 9/2007 | Houde et al. | |
| 7,284,956 B2 | 10/2007 | Nose et al. | |
| 7,288,111 B1 | 10/2007 | Holloway et al. | |
| 7,290,929 B2 | 11/2007 | Smith et al. | |
| 7,329,236 B2 | 2/2008 | Keren et al. | |
| 7,331,921 B2 | 2/2008 | Viole et al. | |
| 7,335,192 B2 | 2/2008 | Keren et al. | |
| 7,341,570 B2 | 3/2008 | Keren et al. | |
| 7,381,179 B2 | 6/2008 | Aboul-Hosn et al. | |
| 7,393,181 B2 | 7/2008 | McBride et al. | |
| 7,469,716 B2 | 12/2008 | Parrino et al. | |
| 7,491,163 B2 | 2/2009 | Viole et al. | |
| 7,534,258 B2 | 5/2009 | Gomez et al. | |
| 7,605,298 B2 | 10/2009 | Bechert et al. | |
| 7,619,560 B2 | 11/2009 | Penna et al. | |
| 7,633,193 B2 | 12/2009 | Masoudipour et al. | |
| 7,645,225 B2 | 1/2010 | Medvedev et al. | |
| 7,682,673 B2 | 3/2010 | Houston et al. | |
| 7,722,568 B2 | 5/2010 | Lenker et al. | |
| 7,731,675 B2 | 6/2010 | Aboul-Hosn et al. | |
| 7,736,296 B2 | 6/2010 | Siess et al. | |
| 7,758,521 B2 | 7/2010 | Morris et al. | |
| 7,766,892 B2 | 8/2010 | Keren et al. | |
| 7,780,628 B1 | 8/2010 | Keren et al. | |
| 7,785,246 B2 | 8/2010 | Aboul-Hosn et al. | |
| 7,811,279 B2 | 10/2010 | John | |
| 7,819,833 B2 | 10/2010 | Ainsworth et al. | |
| 7,828,710 B2 | 11/2010 | Shifflette | |
| 7,841,976 B2 | 11/2010 | McBride et al. | |
| 7,878,967 B1 | 2/2011 | Khanal | |
| 7,918,828 B2 | 4/2011 | Lundgaard et al. | |
| 7,927,068 B2 | 4/2011 | McBride et al. | |
| 7,942,804 B2 | 5/2011 | Khaw | |
| 7,942,844 B2 | 5/2011 | Moberg et al. | |
| 7,955,365 B2 | 6/2011 | Doty | |
| 7,993,259 B2 | 8/2011 | Kang et al. | |
| 7,998,054 B2 | 8/2011 | Bolling | |
| 7,998,190 B2 | 8/2011 | Gharib et al. | |
| 8,012,079 B2 | 9/2011 | Delgado, III et al. | |
| 8,025,647 B2 | 9/2011 | Siess et al. | |
| 8,079,948 B2 | 12/2011 | Shifflette | |
| 8,110,267 B2 | 2/2012 | Houston et al. | |
| 8,114,008 B2 | 2/2012 | Hidaka et al. | |

(56) References Cited

U.S. PATENT DOCUMENTS

| | | |
|---|---|---|
| 8,123,669 B2 | 2/2012 | Siess et al. |
| 8,177,703 B2 | 5/2012 | Smith et al. |
| 8,206,350 B2 | 6/2012 | Mann et al. |
| 8,216,122 B2 | 7/2012 | Kung et al. |
| 8,236,040 B2 | 8/2012 | Mayberry et al. |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,333,687 B2 | 12/2012 | Farnan et al. |
| 8,364,278 B2 | 1/2013 | Pianca et al. |
| 8,376,707 B2 | 2/2013 | McBride et al. |
| 8,388,565 B2 | 3/2013 | Shifflette |
| 8,414,645 B2 | 4/2013 | Dwork et al. |
| 8,439,859 B2 | 5/2013 | Pfeffer et al. |
| 8,485,961 B2 | 7/2013 | Campbell et al. |
| 8,535,211 B2 | 9/2013 | Campbell et al. |
| 8,597,170 B2 | 12/2013 | Walters et al. |
| 8,617,239 B2 | 12/2013 | Reitan |
| 8,684,904 B2 | 4/2014 | Campbell et al. |
| 8,690,749 B1 | 4/2014 | Nunez |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | Larose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,634 B2 | 7/2015 | Schumacher et al. |
| 9,089,670 B2 | 7/2015 | Scheckel |
| 9,217,442 B2 | 12/2015 | Wiessler et al. |
| 9,308,302 B2 | 4/2016 | Zeng |
| 9,314,558 B2 | 4/2016 | Er |
| 9,327,067 B2 | 5/2016 | Zeng et al. |
| 9,328,741 B2 | 5/2016 | Liebing |
| 9,358,330 B2 | 6/2016 | Schumacher |
| 2001/0004681 A1 | 6/2001 | Landau |
| 2002/0107506 A1 | 8/2002 | McGuckin et al. |
| 2002/0111663 A1 | 8/2002 | Dahl et al. |
| 2003/0018380 A1 | 1/2003 | Craig et al. |
| 2003/0100819 A1 | 5/2003 | Siess |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2004/0073141 A1* | 4/2004 | Hartley ............... A61M 25/09 600/585 |
| 2005/0015007 A1* | 1/2005 | Itou .................. A61M 25/0041 606/108 |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0113631 A1 | 5/2005 | Bolling et al. |
| 2005/0135942 A1 | 6/2005 | Arnold et al. |
| 2005/0137680 A1 | 6/2005 | Ortiz et al. |
| 2005/0165269 A9 | 7/2005 | Aboul-Hosn et al. |
| 2005/0250975 A1 | 11/2005 | Carrier et al. |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0233270 A1 | 10/2007 | Weber et al. |
| 2008/0004645 A1 | 1/2008 | To et al. |
| 2008/0004690 A1 | 1/2008 | Robaina |
| 2008/0031953 A1 | 2/2008 | Takakusagi et al. |
| 2008/0103442 A1 | 5/2008 | Kesten et al. |
| 2008/0103516 A1 | 5/2008 | Wulfman et al. |
| 2008/0103591 A1 | 5/2008 | Siess |
| 2008/0119943 A1 | 5/2008 | Armstrong et al. |
| 2008/0132748 A1 | 6/2008 | Shifflette |
| 2008/0167679 A1 | 7/2008 | Papp |
| 2008/0275290 A1 | 11/2008 | Viole et al. |
| 2008/0306327 A1* | 12/2008 | Shifflette ............ A61M 60/414 600/16 |
| 2009/0018567 A1 | 1/2009 | Escudero et al. |
| 2009/0023975 A1 | 1/2009 | Marseille et al. |
| 2009/0024085 A1 | 1/2009 | To et al. |
| 2009/0093764 A1 | 4/2009 | Pfeffer et al. |
| 2009/0093765 A1 | 4/2009 | Glenn |
| 2009/0093796 A1* | 4/2009 | Pfeffer ................. A61M 60/13 600/16 |
| 2009/0099638 A1 | 4/2009 | Grewe |
| 2009/0112312 A1 | 4/2009 | Larose et al. |
| 2009/0118567 A1 | 5/2009 | Siess |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2009/0234378 A1 | 9/2009 | Escudero et al. |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0057050 A1* | 3/2010 | Webler, Jr. ........ A61M 25/0054 604/525 |
| 2010/0087773 A1 | 4/2010 | Ferrari |
| 2010/0127871 A1 | 5/2010 | Pontin |
| 2010/0197994 A1 | 8/2010 | Mehmanesh |
| 2010/0210895 A1 | 8/2010 | Aboul-Hosn et al. |
| 2010/0241008 A1* | 9/2010 | Belleville ............ A61B 5/0215 600/478 |
| 2010/0268017 A1 | 10/2010 | Siess |
| 2010/0274330 A1 | 10/2010 | Burwell et al. |
| 2010/0286210 A1 | 11/2010 | Murata et al. |
| 2010/0286791 A1 | 11/2010 | Goldsmith |
| 2010/0324567 A1* | 12/2010 | Root .................. A61M 25/0026 606/108 |
| 2011/0004046 A1 | 1/2011 | Campbell et al. |
| 2011/0004049 A1 | 1/2011 | Yi et al. |
| 2011/0004291 A1 | 1/2011 | Davis et al. |
| 2011/0021865 A1 | 1/2011 | Aboul-Hosn et al. |
| 2011/0034874 A1 | 2/2011 | Reitan et al. |
| 2011/0040140 A1 | 2/2011 | Shifflette |
| 2011/0071338 A1 | 3/2011 | McBride et al. |
| 2011/0076439 A1 | 3/2011 | Zeilon |
| 2011/0152906 A1 | 6/2011 | Escudero et al. |
| 2011/0152907 A1 | 6/2011 | Escudero et al. |
| 2011/0237863 A1 | 9/2011 | Ricci et al. |
| 2011/0257462 A1 | 10/2011 | Rodefeld et al. |
| 2011/0270182 A1 | 11/2011 | Breznock et al. |
| 2011/0275884 A1 | 11/2011 | Scheckel |
| 2012/0004495 A1 | 1/2012 | Bolling et al. |
| 2012/0029265 A1 | 2/2012 | Larose et al. |
| 2012/0059213 A1 | 3/2012 | Spence et al. |
| 2012/0059460 A1* | 3/2012 | Reitan ................ A61M 60/216 623/3.12 |
| 2012/0093628 A1* | 4/2012 | Liebing ............... A61M 60/825 415/140 |
| 2012/0142994 A1 | 6/2012 | Toellner |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0203056 A1 | 8/2012 | Corbett |
| 2012/0224970 A1 | 9/2012 | Schumacher et al. |
| 2012/0226097 A1 | 9/2012 | Smith et al. |
| 2012/0234411 A1 | 9/2012 | Scheckel |
| 2012/0245404 A1 | 9/2012 | Smith et al. |
| 2012/0265002 A1* | 10/2012 | Roehn ................ A61M 60/857 600/16 |
| 2013/0041202 A1 | 2/2013 | Toellner et al. |
| 2013/0053622 A1 | 2/2013 | Corbett |
| 2013/0053623 A1 | 2/2013 | Evans et al. |

(56) References Cited

U.S. PATENT DOCUMENTS

| | | | |
|---|---|---|---|
| 2013/0060077 A1* | 3/2013 | Liebing | A61M 60/135 600/16 |
| 2013/0066140 A1 | 3/2013 | McBride et al. | |
| 2013/0085318 A1 | 4/2013 | Toellner | |
| 2013/0096364 A1 | 4/2013 | Reichenbach et al. | |
| 2013/0103063 A1 | 4/2013 | Escudero et al. | |
| 2013/0106212 A1 | 5/2013 | Nakazumi et al. | |
| 2013/0129503 A1 | 5/2013 | McBride et al. | |
| 2013/0138205 A1 | 5/2013 | Kushwaha et al. | |
| 2013/0204362 A1 | 8/2013 | Toellner et al. | |
| 2013/0209292 A1 | 8/2013 | Baykut et al. | |
| 2013/0237744 A1 | 9/2013 | Pfeffer et al. | |
| 2013/0237962 A1* | 9/2013 | Kawai | A61M 25/0068 604/524 |
| 2013/0245360 A1 | 9/2013 | Schumacher | |
| 2013/0303830 A1 | 11/2013 | Zeng et al. | |
| 2013/0303969 A1 | 11/2013 | Keenan et al. | |
| 2013/0303970 A1 | 11/2013 | Keenan et al. | |
| 2013/0331639 A1 | 12/2013 | Campbell et al. | |
| 2013/0345492 A1 | 12/2013 | Pfeffer et al. | |
| 2014/0005467 A1 | 1/2014 | Farnan et al. | |
| 2014/0010686 A1 | 1/2014 | Tanner et al. | |
| 2014/0012065 A1 | 1/2014 | Fitzgerald et al. | |
| 2014/0025041 A1* | 1/2014 | Fukuoka | A61M 25/00 604/523 |
| 2014/0039465 A1 | 2/2014 | Heike et al. | |
| 2014/0051908 A1 | 2/2014 | Khanal et al. | |
| 2014/0067057 A1 | 3/2014 | Callaway et al. | |
| 2014/0088455 A1 | 3/2014 | Christensen et al. | |
| 2014/0148638 A1 | 5/2014 | Larose et al. | |
| 2014/0163664 A1 | 6/2014 | Goldsmith | |
| 2014/0255176 A1 | 9/2014 | Bredenbreuker et al. | |
| 2014/0275725 A1 | 9/2014 | Schenck et al. | |
| 2014/0275726 A1 | 9/2014 | Zeng | |
| 2014/0301822 A1 | 10/2014 | Scheckel | |
| 2014/0303596 A1 | 10/2014 | Schumacher et al. | |
| 2015/0025558 A1 | 1/2015 | Wulfman et al. | |
| 2015/0031936 A1 | 1/2015 | Larose et al. | |
| 2015/0051435 A1 | 2/2015 | Siess et al. | |
| 2015/0051436 A1 | 2/2015 | Spanier et al. | |
| 2015/0080743 A1 | 3/2015 | Siess et al. | |
| 2015/0087890 A1 | 3/2015 | Spanier et al. | |
| 2015/0141738 A1 | 5/2015 | Toellner et al. | |
| 2015/0141739 A1 | 5/2015 | Hsu et al. | |
| 2015/0151032 A1 | 6/2015 | Voskoboynikov et al. | |
| 2015/0209498 A1 | 7/2015 | Franano et al. | |
| 2015/0250935 A1 | 9/2015 | Anderson et al. | |
| 2015/0290372 A1 | 10/2015 | Muller et al. | |
| 2015/0343179 A1 | 12/2015 | Schumacher et al. | |
| 2016/0184500 A1 | 6/2016 | Zeng | |
| 2016/0250399 A1 | 9/2016 | Tiller et al. | |
| 2016/0250400 A1 | 9/2016 | Schumacher | |
| 2016/0256620 A1 | 9/2016 | Scheckel et al. | |
| 2016/0303299 A1 | 10/2016 | Muller et al. | |

FOREIGN PATENT DOCUMENTS

| | | |
|---|---|---|
| CA | 2367469 A1 | 10/2000 |
| CA | 2407938 A1 | 11/2001 |
| CA | 2480467 A1 | 8/2003 |
| CA | 2701810 A1 | 4/2009 |
| DE | 19613565 C1 | 7/1997 |
| EP | 0364293 A2 | 4/1990 |
| EP | 0453234 A1 | 10/1991 |
| EP | 0533432 A1 | 3/1993 |
| EP | 1207934 A2 | 5/2002 |
| EP | 1393762 A1 | 3/2004 |
| EP | 1591079 A1 | 11/2005 |
| EP | 2151257 A1 | 2/2010 |
| EP | 2263732 A2 | 12/2010 |
| EP | 2298374 A1 | 3/2011 |
| FR | 2267800 A1 | 11/1975 |
| GB | 2239675 A | 7/1991 |
| JP | S48-23295 | 3/1973 |
| JP | S58190448 A | 11/1983 |
| JP | H06114101 A | 4/1994 |
| JP | H08500512 A | 1/1996 |
| JP | H08501466 A | 2/1996 |
| JP | H10099447 | 4/1998 |
| JP | 2002505168 A | 2/2002 |
| JP | 2004514506 A | 5/2004 |
| JP | 2011-000620 | 9/2005 |
| JP | 2011-157961 | 8/2011 |
| TW | 500877 B | 9/2002 |
| WO | 8904644 | 6/1989 |
| WO | 8905164 A1 | 6/1989 |
| WO | 9405347 | 3/1994 |
| WO | 9406486 | 3/1994 |
| WO | 9526695 A2 | 10/1995 |
| WO | 9715228 A1 | 5/1997 |
| WO | 9737697 A1 | 10/1997 |
| WO | 9900368 | 1/1999 |
| WO | 9902204 | 1/1999 |
| WO | 9916387 | 4/1999 |
| WO | 9937352 | 7/1999 |
| WO | 9944651 | 9/1999 |
| WO | 9944670 | 9/1999 |
| WO | 9959652 | 11/1999 |
| WO | 9965546 | 12/1999 |
| WO | 00012148 | 3/2000 |
| WO | 00019097 A1 | 4/2000 |
| WO | 00108448 A2 | 4/2000 |
| WO | 00037139 A1 | 6/2000 |
| WO | 00038591 A2 | 7/2000 |
| WO | 00041612 A2 | 7/2000 |
| WO | 00043053 A1 | 7/2000 |
| WO | 00043062 A1 | 7/2000 |
| WO | 00045874 A1 | 8/2000 |
| WO | 00061207 A1 | 10/2000 |
| WO | 00069489 A1 | 11/2000 |
| WO | 01117581 A2 | 3/2001 |
| WO | 01024867 A1 | 4/2001 |
| WO | 01083016 | 11/2001 |
| WO | 02043791 | 6/2002 |
| WO | 02070039 A2 | 9/2002 |
| WO | 03048582 | 6/2003 |
| WO | 03068303 | 8/2003 |
| WO | 03070299 | 8/2003 |
| WO | 03103745 A2 | 12/2003 |
| WO | 2005089674 A1 | 9/2005 |
| WO | 2005123158 A1 | 12/2005 |
| WO | 2006046779 | 5/2006 |
| WO | 2006051023 | 5/2006 |
| WO | 2007112033 | 10/2007 |
| WO | 2008034068 | 3/2008 |
| WO | 2009073037 A1 | 6/2009 |
| WO | 2009076460 A2 | 6/2009 |
| WO | 2010063494 A1 | 6/2010 |
| WO | 2010127871 A1 | 11/2010 |
| WO | 2010133567 A1 | 11/2010 |
| WO | 2010149393 A1 | 12/2010 |
| WO | 2011035926 A1 | 3/2011 |
| WO | 2011035927 | 3/2011 |
| WO | 2011035929 A2 | 3/2011 |
| WO | 2011039091 A1 | 4/2011 |
| WO | 2011076439 A1 | 6/2011 |
| WO | 2011089022 A1 | 7/2011 |
| WO | 01078807 | 10/2011 |
| WO | 2012007140 | 1/2012 |
| WO | 2012007141 | 1/2012 |
| WO | 2012064525 | 7/2012 |
| WO | 2012094534 | 7/2012 |
| WO | 2013148697 A1 | 10/2013 |
| WO | 2013160407 A1 | 10/2013 |
| WO | 2013073245 | 11/2013 |

(56) References Cited

FOREIGN PATENT DOCUMENTS

| WO | 2014019274 A1 | 2/2014 |
|---|---|---|
| WO | 2015063277 A3 | 7/2015 |

OTHER PUBLICATIONS

Abiomed, "Impella 5.0 with the Impella Console, Circulatory Support System, Instructions for Use & Clinical Reference Manual," Jun. 2010, in 122 pages.

Abiomed—Recovering Hearts. Saving Lives., Impella 2.5 System, Instructions for Use, Jul. 2007, in 86 sheets.

Barras et al., "Nitinol—Its Use in Vascular Surgery and Other Applications," Eur. J. Vasc. Endovasc. Surg., 2000, pp. 564-569; vol. 19.

Biscarini et al., "Enhanced Nitinol Properties for Biomedical Applications," Recent Patents on Biomedical Engineering, 2008, pp. 180-196, vol. 1 (3).

Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.

Duerig et al., "An Overview of Nitinol Medical Applications," Materials Science Engineering, 1999, pp. 149-160; vol. A273.

Extended European Search Report received in European Patent Application No. 07753903.9, dated Oct. 8, 2012, in 7 pages (THOR. 034VEP).

European Search Report received in European Patent Application No. 05799883.3, dated May 10, 2011, in 4 pages.

Grech, "Percutaneous Coronary Intervention. I: History and Development," BMJ., May 17, 2003, pp. 1080-1082, vol. 326.

Hsu et al., "Review of Recent Patents on Foldable Ventricular Assist Devices," Recent Patents on Biomedical Engineering, 2012, pp. 208-222, vol. 5.

Ide et al., "Evaluation of the Pulsatility of a New Pulsatile Left Ventricular Assist Device—the Integrated Cardioassist Catheter—in Dogs," J. of Thorac and Cardiovasc Sur, Feb. 1994, pp. 569-0575, vol. 107(2).

Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, pp. 286-290, vol. 16(3).

International Search Report received in International Patent Application No. PCT/US2003/004853, dated Jul. 3, 2003, in 3 pages.

International Search Report and Written Opinion received in International Patent Application No. PCT/US2012/020369, dated Jul. 30, 2012, in 10 pages.

International Search Report and Written Opinion received in International Patent Application No. PCT/US2012/020382, dated Jul. 31, 2012, in 11 pages.

International Search Report and Written Opinion received in International Patent Application No. PCT/US2012/020553, dated Aug. 17, 2012, in 8 pages.

International Search Report and Written Opinion received in International Patent Application No. PCT/US2012/020383, dated Aug. 17, 2012, in 9 pages.

International Preliminary Examination Report received in International Patent Application No. PCT/US2003/04853, dated Jul. 26, 2004, in 5 pages.

International Preliminary Examination Report received in International Patent Application No. PCT/US2003/04401, dated May 18, 2004, in 4 pages.

International Search Report received in International Patent Application No. PCT/US2003/004401, dated Nov. 10, 2003, in 9 pages.

International Search Report and Written Opinion received in International Patent Application No. PCT/US2005/033416, dated Dec. 11, 2006, in 8 pages.

International Search Report and Written Opinion received in International Patent Application No. PCT/US2013/040798, dated Aug. 21, 2013, in 16 pages.

International Search Report and Written Opinion received in International Patent Application No. PCT/US2013/040799, dated Aug. 21, 2013, in 19 pages.

International Search Report and Written Opinion received in International Patent Application No. PCT/US2013/040809, dated Sep. 2, 2013, in 25 pages.

International Search Report and Written Opinion received in International Patent Application No. PCT/US2013/048343, dated Oct. 11, 2013, in 15 pages.

International Search Report and Written Opinion received in International Patent Application No. PCT/US2013/048332, dated Oct. 16, 2013, in 17 pages.

International Preliminary Report on Patentability and Written Opinion of the International Searching Authority received in International Patent Application No. PCT/US2005/033416, dated Mar. 20, 2007, in 7 pages.

International Preliminary Report on Patentability and Written Opinion of the International Searching Authority received in International Patent Application No. PCT/US2007/007313, dated Sep. 23, 2008, in 6 pages.

International Search Report and Written Opinion received in International Patent Application No. PCT/US2007/007313, dated Mar. 4, 2008, in 6 pages.

International Search Report Written Opinion received in International Patent Application No. PCT/US2010/040847, dated Dec. 14, 2010, in 17 pages.

Krishnamani et al., "Emerging Ventricular Assist Devices for Long-Term Cardiac Support," National Review, Cardiology, Feb. 2010, pp. 71-76, vol. 7.

Mihaylov et al., "Development of a New Introduction Technique for the Pulsatile Catheter Pump," Artificial Organs, 1997, pp. 425-427; vol. 21 (5).

Mihaylov et al., "Evaluation of the Optimal Driving Mode During Left Ventricular Assist with Pulsatile Catheter Pump in Calves," Artificial Organs, 1999, pp. 1117-1122; vol. 23(12).

Morgan, "Medical Shape Memory Alloy Applications—The Market and its Products," Materials Science and Engineering, 2004, pp. 16-23, vol. A 378.

Morsink et al., "Numerical Modelling of Blood Flow Behaviour in the Valved Catheter of the PUCA-Pump, a LVAD," The International Journal of Artificial Organs, 1997, pp. 277-284; vol. 20(5).

Nishimura et al, "The Enabler Cannula Pump: A Novel Circulatory Support System," The International Journal of Artificial Organs, 1999, pp. 317-323; vol. 22(5).

Petrini et al., "Biomedical Applications of Shape Memory Alloys," Journal of Metallurgy, 2011, pp. 1-15.

Raess et al., "Impella 2.5," J. Cardiovasc. Transl. Res., 2009, pp. 168-172, vol. 2(2).

Rakhorst et al., "In Vitro Evaluation of the Influence of Pulsatile Intraventricular Pumping on Ventricular Pressure Patterns," Artificial Organs, 1994, pp. 494-499, vol. 18(7).

Reitan et al., "Hydrodynamic Properties of a New Percutaneous Intra-Aortic Axial Flow Pump," ASAIO Journal2000, pp. 323-328.

Reitan et al., "Hemodynamic Effects of a New Percutaneous Circulatory Support Device in a Left Ventricular Failure Model," ASAIO Journal, 2003, pp. 731-736, vol. 49.

Schmitz-Rode et al., "An Expandable Percutaneous Catheter Pump for Left Ventricular Support," Journal of the American College of Cardiology, 2005, pp. 1856-1861, vol. 45(11).

Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.

Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).

Sharony et al., "Right Heart Support During Off-Pump Coronary Artery Surgery—A Multi-Center Study," The Heart Surgery Forum, 2002, pp. 13-16, vol. 5(1).

Smith et al., "First-In-Man Study of the Reitan Catheter Pump for Circulatory Support in Patients Undergoing High-Risk Percutane-

(56) References Cited

OTHER PUBLICATIONS ous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
"Statistical Analysis and Clinical Experience with the Recover® Pump Systems", Impella CardioSystems GmbH, Sep. 2005, 2 sheets.
Stoeckel et al., "Self-Expanding Nitinol Stents—Material and Design Considerations," European Radiology, 2003, in 13 sheets.
Supplemental European Search Report received from the European Patent Office in EP Application No. EP 05799883 dated Mar. 19, 2010, 3 pages.
Takagaki et al., "A Novel Miniature Ventricular Assist Device for Hemodynamic Support," ASAIO Journal, 2001, pp. 412-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1 (4).
Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).
Verkerke et al., "Numerical Simulation of the Pulsating Catheter Pump: A Left Ventricular Assist Device," Artificial Organs, 1999, pp. 924-931, vol. 23(10).
Verkerke et al., "The PUCA Pump: A Left Ventricular Assist Device," Artificial Organs, 1993, pp. 365-368, vol. 17(5).
Wampler et al., "The Sternotomy Hemopump, A Second Generation Intraarterial Ventricular Assist Device," ASAIO Journal, 1993, pp. M218-M223, vol. 39.
Written Opinion received in International Patent Application No. PCT/US2003/04853, dated Feb. 25, 2004, 5 pages.
Food and Drug Administration 510(k) Summary for Predicate Device Impella 2.5 (K112892), prepared Sep. 5, 2012.
International Search Report and Written Opinion received in International Patent Application No. PCT/US2014/020878, dated May 7, 2014, in 13 pages.
Stolinski et al., "The heart-pump interaction: effects of a microaxial blood pump," International Journal of Artificial Organs, 2002, pp. 1082-1088, vol. 25, Issue 11.
Weber et al., "Principles of Impella Cardiac Support," Supplemental to Cardiac Interventions Today, Aug./Sep. 2009.
Kunst et al., "Integrated unit for programmable control of the 21 F Hemopump and registration of physiological signals," Medical & Biological Engineering Computing, Nov. 1994, pp. 694-696.
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
Aboul-Hosn et al., "The Hemopump: Clinical Results and Future Applications", Assisted Circulation 4, 1995, in 14 pages.
Compendium of Technical and Scientific Information for the Hemopump Temporary Cardiac Assist System, Johnson & Johnson Interventional Systems, 1988, in 15 pages.
Dekker et al., "Efficacy of a New Intraaortic Propeller Pump vs the Intraaortic Balloon Pump, An Animal Study", Chest, Jun. 2003, vol. 123, No. 6, pp. 2089-2095.
Impella CP®—Instructions for Use & Clinical Reference Manual (United States only), Abiomed, Inc., Jul. 2014, 148 pages, www.abiomed.com.
Impella LD® with the Impella® Controller—Circulatory Support System—Instructions for Use & Clinical Reference Manual (United States only), Abiomed, Inc., Sep. 2010, 132 pages, www.abiomed.com.
International Preliminary Report on Patentability and Written Opinion received in International Patent Application No. PCT/US2014/020878, dated Sep. 15, 2015, in 8 pages.
International Search Reort and Written Opinion received in International Patent Application No. PCT/US2015/026013, dated Jul. 8, 2015, in 12 pages.
International Search Report and Written Opinion received in International Patent Application No. PCT/US2015/026014, dated Jul. 15, 2015, in 13 pages.
International Search Report and Written Opinion received in International Patent Application No. PCT/US2015/026025, dated Jul. 20, 2015, in 12 pages.
International Search Report and Written Opinion received in International Patent Application No. PCT/US2015/025959, dated Aug. 28, 2015, in 16 pages.
International Search Report and Written Opinion received in International Patent Application No. PCT/US2015/025960, dated Sep. 3, 2015, in 15 pages.
International Search Report and Written Opinion received in International Patent Application No. PCT/US2015/045370, dated Nov. 18, 2015, in 12 pages.
Jomed Reitan Catheter Pump RCP, Percutaneous Circulatory Support, in 10 pages, believed to be published prior to Oct. 15, 2003.
Jomed Reitan Catheter Pump RCP, Feb. 18, 2003, in 4 pages.
Minimally Invasive Cardiac Assist Jomed Catheter PumpTM, in 6 pages, believed to be published prior to Jun. 16, 1999.
Reitan, Evaluation of a New Percutaneous Cardiac Assist Device, Department of Cardiology, Faculty of Medicine, Lund University, Sweden, 2002, in 172 pages.
Siess et al., "Hydraulic refinement of an intraarterial microaxial blood pump", The International Journal of Artificial Organs, 1995, vol. 18, No. 5, pp. 273-285.
Siess, "Systemanalyse und Entwicklung intravasaler Rotationspumpen zur Herzunterstlitzung", Helmholtz-Institut fur Blomedixinische Technik an der RWfH Aachen, Jun. 24, 1998, in 105 pages.
Siess et al., "Basic design criteria for rotary blood pumps," H. Masuda, Rotary Blood Pumps, Springer, Japan,2000, pp. 69-83.
Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Siess et al., "From a lab type to a product: A retrospective view on Impella's assist technology," Artificial Organs, 2001, pp. 414-421, vol. 25, No. 5, Blackwell Science, Inc., International Society for Artificial Organs.
Siess et al., "System analysis and development of intravascular rotation pumps for cardiac assist," Dissertation, Shaker Verlag, Aachen, 1999, 39 pages.
Extended European Search Report received in European Patent Application No. 13790890.1, dated Jan. 7, 2016, in 6 pages (THOR.089EP).
Extended European Search Report received in European Patent Application No. 13791118.6, dated Jan. 7, 2016, in 6 pages (THOR.072EP).
Extended European Search Report received in European Patent Application No. 13813687.4, dated Feb. 24, 2016, in 6 pages (THOR.093EP).
Extended European Search Report received in European Patent Application No. 13813687.2, dated Feb. 26, 2016, in 6 pages (THOR.092EP).
International Search Report and Written Opinion received in International Patent Application No. PCT/US2016/014371, dated May 2, 2016, in 18 pages.
International Search Report and Written Opinion received in International Patent Application No. PCT/US2016/014379, dated Jul. 25, 2016, in 19 pages.
International Search Report and Written Opinion received in International Patent Application No. PCT/US2016/014391, dated May 2, 2016, in 17 pages.
Nullity Action against the owner of the German part DE 50 2007 005 015.6 of European patent EP 2 04 7 872 81, dated Jul. 13, 2015, in 61 pages.
Extended European Search Report received in European Patent Application No. 14 779928.2, dated Oct. 7, 2016, in 6 pages (THOR.084EP).

(56) References Cited

OTHER PUBLICATIONS

Extended European Search Report received in European Patent Application No. 14 764392.8, dated Oct. 27, 2016, in 7 pages (THOR.097EP).
International Search Report and Written Opinion received in International Patent Application No. PCT/US2016/051553, dated Feb. 8, 2017, in 15 pages.
Schmitz-Rode et al., "Axial flow catheter pump for circulatory support," Biomedizinische Technik, 2002, Band 47, Erganzungsband 1, Teil 1, pp. 142-143.
International Search Report and Written Opinion for International Patent Application No. PCT/US2017/061446, dated Apr. 17, 2018, 19 pages.

* cited by examiner

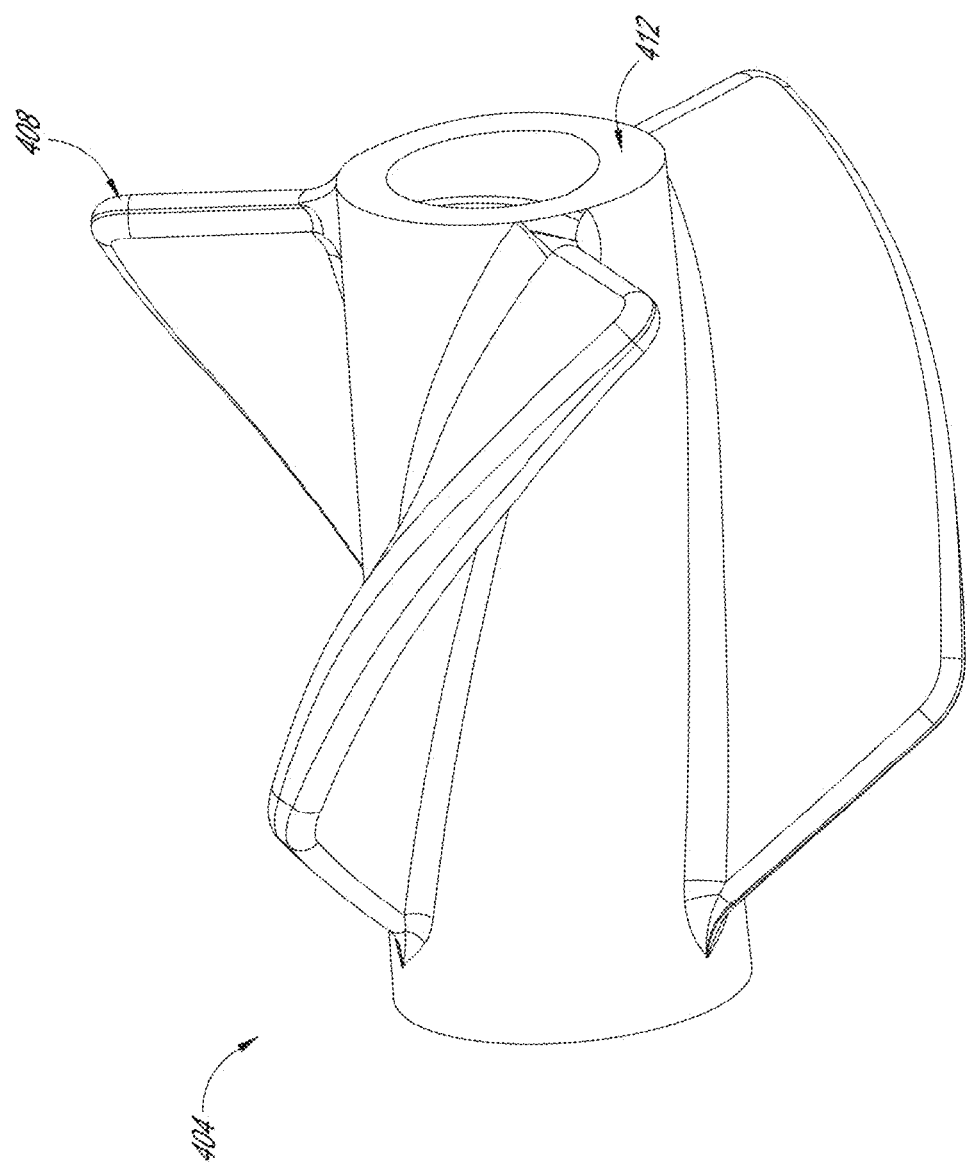

SHEATH ASSEMBLY FOR CATHETER PUMP

CROSS REFERENCE TO RELATED APPLICATIONS

This application claims priority to U.S. patent application Ser. No. 15/812,471, filed Nov. 14, 2017, which claims priority to provisional Application No. 62/421,930, filed Nov. 14, 2016, and which is a continuation-in-part of U.S. patent application Ser. No. 13/801,833, filed Mar. 13, 2013, each of which is incorporated herein by reference in their entireties.

BACKGROUND

Field of the Invention

This application is directed to a catheter pump for mechanical circulatory support of a heart, and related components, systems and methods. In particular, this application is directed to reliable coupling of components that are subject to dynamic loads applied between a plurality of catheter bodies.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e. higher flow). Rotary pumps have become more common recently for treating heart failure. A rotary blood pump is typically inserted into the body and connected to the cardiovascular system, for example, to the left ventricle and the ascending aorta to assist the pumping function of the heart. Other known applications include pumping venous blood from the right ventricle to the pulmonary artery for support of the right side of the heart. An aim of acute circulatory support devices is to reduce the load on the heart muscle for a period of time, to stabilize the patient prior to heart transplant or for continuing support. Rotary blood pumps generally utilize an electric motor which drives an impeller pump at relatively high speeds. In the case where the pump is remote from the motor, for example where the impeller is in the body and the motor is outside the body, there is a need for a robust and reliable connection between the motor and the impeller. There may also be the need for forming a flexible connection between the motor shaft and the impeller to allow free movement of various pump components during use and when pushing through the vasculature to the treatment location. There is also the continuing need to provide these system components in a compact, efficient form factor to allow for percutaneous approaches.

There is a need for improved mechanical circulatory support devices for treating acute heart failure. Fixed cross-section ventricular assist devices designed to provide partial or near full heart flow rate are either too large to be advanced percutaneously (e.g., through the femoral artery without a cutdown) or provide insufficient flow.

SUMMARY OF THE INVENTION

In one embodiment, a catheter pump includes a catheter body having at least one lumen therethrough, and comprising a distal end and a proximal end. An expandable impeller assembly includes an expandable impeller and an expandable cannula coupled to the distal end of the catheter body and housing the expandable impeller, the expandable cannula comprising a substantially straight segment having a distal inlet and a proximal outlet, the substantially straight segment configured to straddle an aortic valve. The catheter body comprises a proximal vessel contact zone and a distal vessel contact zone that are each proximal to the substantially straight segment, the proximal vessel contact zone and distal vessel contact zone configured to provide a force against an aortic arch to stabilize the expandable impeller assembly across the aortic valve.

In another embodiment, a catheter pump assembly is disclosed. The catheter pump assembly can include a pump including an impeller assembly and a catheter body disposed proximal to and supporting the pump. The catheter body can include relatively hard sections adjacent to a relatively softer middle section such that the middle section is configured to contact a wall of an aorta of a patient. The catheter body can include relatively hard sections adjacent to a relatively softer middle section such that the middle section facilitates bending relative to the relatively hard sections. The catheter body can include relatively hard sections adjacent to a relatively softer middle section such that when the pump assembly is positioned at a target location (e.g. across a valve), the middle section is configured to bend and the relatively hard sections are configured to remain substantially straight.

In another embodiment, a catheter pump assembly is disclosed. The catheter pump assembly can include a pump including an impeller assembly. A catheter body can be disposed proximally of and configured to couple with the impeller assembly, the catheter body having a vessel wall contact surface, the catheter body configured to cause the vessel wall contact surface to bear against an outer radius of an aortic arch. A bending section can be disposed between the vessel wall contact surface and the impeller assembly, the bending section being more flexible than the catheter body at the location of the vessel wall contact surface such that loads applied distal the vessel wall contact surface result in flexing at the bending section.

In another embodiment, a method is disclosed. The method can include advancing a distal portion of a catheter assembly including an impeller assembly and a catheter body to a treatment location of a patient. The method can include contacting an outer surface of the catheter body with a contact zone of an inner wall of an aorta of the patient to secure at least the distal portion of the catheter assembly against the aorta of the patient, the inner wall being located adjacent to the junction of the ascending aorta and the aortic arch. The method can include activating the impeller assembly to pump blood across the aortic valve. The method can include maintaining the contact between the outer surface of the catheter body and the contact zone while the impeller assembly is activated.

An aspect of at least one of the embodiments disclosed herein is the realization that the connection of a flexible proximal body to a more rigid distal segment of a catheter assembly can be better secured with an robust mechanical interface between one or more features of these components. For example, a distal end of the flexible proximal body can be fitted with a device or structure providing an interface that mechanically engages the flexible proximal body and that can be directly joined, e.g. welded, to a structure to which a load is applied.

In one embodiment, a catheter pump assembly is provided that includes an elongate polymeric catheter body, a cannula, and a tubular interface. The elongate polymeric catheter body has a proximal end and a distal end. The cannula has an expandable portion disposed distally of the elongate polymeric catheter body. The cannula can also have another tubular portion that is proximal to the distal portion. The tubular interface has an outer surface configured to be joined to the tubular portion of the cannula and an inner surface. The inner surface is disposed over the distal end of the elongate polymeric catheter body. The tubular interface has a plurality of transverse channels extending outward from the inner surface of the tubular interface. An outer surface of the elongate polymeric catheter body projects into the transverse channels to mechanically integrate the elongate polymeric catheter body with the tubular interface.

In another embodiment, a catheter pump assembly is provided that includes an elongate polymeric catheter body, a tubular member, and a mechanical interface. The elongate polymeric catheter body has a proximal end and a distal end. At least a portion of the tubular member is disposed distally of the elongate polymeric catheter body. The mechanical interface is disposed between a portion of the elongate polymeric catheter body and the tubular member. The mechanical interface is configured to mechanically integrate with a surface of the elongate polymeric catheter body.

In another embodiment, a catheter pump assembly is provided that includes an elongate catheter body, a metallic tubular member, and first and second mechanical interfaces. The elongate catheter body has a proximal portion and a distal portion. The metallic tubular member is disposed at least partially distally of the elongate catheter body. The first mechanical interface has a first portion joined to the distal portion of the elongate catheter body and a second portion welded to the metallic tubular member. The second mechanical interface is disposed on an outside surface of the catheter pump assembly. The second mechanical interface has a deflectable member configured to be disposed adjacent to the outside surface of the catheter pump assembly in a first configuration. The deflectable member is configured to be disposed inward of the outside surface of the catheter pump assembly in a second configuration. When in the second configuration, the deflectable member mechanically and securely engages the outside surface of the catheter pump assembly with a structure disposed inward of the second mechanical interface.

In another embodiment, a method is provided for coupling components of a catheter pump assembly together. An elongate polymeric tubular body is provided that has a proximal end and a distal end. A metallic tubular body is provided that has a proximal portion and a distal portion. A mechanical interface having a first interface zone and a second interface zone is positioned such that the first interface zone is disposed over a portion of the elongate polymeric tubular body adjacent to the distal end thereof. The polymer is then caused to flow into the first interface zone, whereby the elongate polymeric tubular body becomes joined with the first interface zone of the mechanical interface. The metallic tubular body is coupled with the second interface zone of the mechanical interface.

In one approach, the polymer is caused to flow by heating the elongate polymeric tubular body to cause at least a portion of elongate polymeric tubular body adjacent to the distal end thereof to transition to a state with low resistance to deformation.

In another embodiment, a catheter pump assembly is provided that includes a proximal portion, a distal portion, and a catheter body having a lumen extending therebetween along a longitudinal axis. The catheter pump assembly also includes a torque assembly that has a first portion disposed in the lumen of the catheter body and a second portion disposed distal of the first portion. The second portion coupled with an impeller. The torque assembly causes the impeller to rotate upon rotation of the first portion of the torque assembly. The catheter pump assembly also includes a thrust bearing and a thrust bearing brace. The thrust bearing is disposed within the catheter pump assembly adjacent to the distal end of the catheter body. The thrust bearing resists movement of the torque assembly along the longitudinal axis. The thrust bearing brace is disposed on the outside surface of the torque assembly. The thrust bearing brace has a distal face that is directly adjacent to a proximal face of the thrust bearing.

In another embodiment, a catheter assembly is provided that includes an elongate flexible body, a torque assembly, a bearing assembly, and a sleeve. The elongate flexible body is disposed along a proximal portion of the catheter assembly and has a proximal infusate channel formed therein. The torque assembly extends through the elongate flexible body. The bearing assembly comprises a housing having an outer surface and a bearing surface disposed within the housing. The bearing surface provides for rotation of the torque assembly within the bearing housing. The sleeve comprises and an inner surface configured to be disposed over the outer surface of the housing of the bearing assembly and a fluid communication structure that extends through the walls of the sleeve. The catheter assembly also includes a distal infusate channel in fluid communication with the proximal infusate channel, the distal infusate channel disposed over the outer surface of the bearing housing and through side walls of the slot.

In another embodiment, a catheter pump assembly is provided that includes a proximal portion, a distal portion, and a catheter body having a lumen extending along a longitudinal axis between the proximal and distal portions. The catheter pump assembly also includes an impeller disposed at the distal portion and a stator disposed distal of the impeller to straighten flow downstream from the impeller. The stator is collapsible from a deployed configuration to a collapsed configuration.

In another embodiment, a catheter system is provided that includes an elongate polymeric catheter body, a cannula, and at least one expandable component disposed within the cannula. The elongate polymeric catheter body has a proximal end and a distal end. The cannula has an expandable portion disposed distally of the elongate polymeric catheter body. The catheter system also includes an elongate sheath body that has a retracted position in which the elongate sheath body is proximal of the expandable portion of the cannula and the at least one expandable component and a forward position in which the elongate sheath body is disposed over the expandable portion of the cannula and the at least one expandable component. A first segment of the elongate sheath body disposed over the expandable portion of the cannula and the at least one expandable component is configured to resist kinking to a greater extent than a second segment of the elongate sheath body disposed adjacent to the first segment.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 6D-1 shows an early portion of a method of positioning a catheter assembly of a catheter pump as disclosed herein.

FIG. 6D-2 shows a portion of a method following that shown in FIG. 6D-1 in which a catheter assembly as described herein is advanced through the arterial vasculature until a distal portion thereof is disposed across an aortic valve of a patient.

FIG. 6D-3 shows a portion of a method following that shown in FIG. 6D-2 in which contrast is provided to the aorta from the region of the aortic valve through the aortic arch.

FIG. 6D-4 shows a portion of a method following that shown in FIG. 6D-3 in which an outer sheath of the catheter assembly has been retracted relative to an inner sheath to permit the cannula to expand in preparation for operating the catheter pump including the catheter assembly as disclosed herein.

FIG. 6D-5 shows an enlarged fluoroscopic view of a distal portion of the catheter assembly, showing the distal portion expanded in preparation for operation.

FIGS. 15-17 illustrate features of additional embodiments of catheter assemblies having robust mechanical interface.

More detailed descriptions of various embodiments of components for heart pumps useful to treat patients experiencing cardiac stress, including acute heart failure, are set forth below.

DETAILED DESCRIPTION OF THE PREFERRED EMBODIMENT

A high performance catheter pump is desired to provide sufficient output to approach and in some cases exceed natural heart output. Performance of this nature can be achieved with inventive components disclosed herein.

Figure 1:
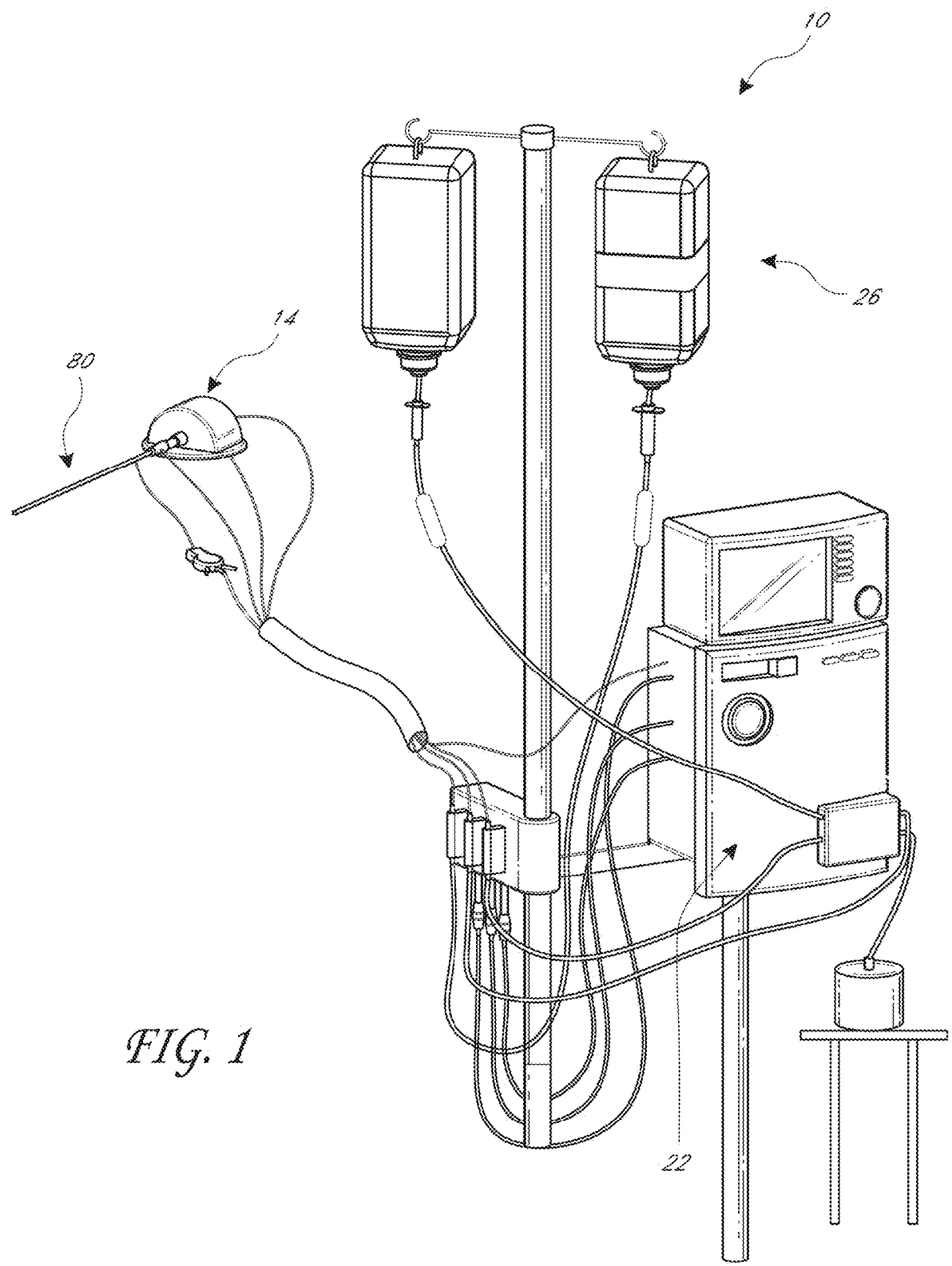
FIG. 1 illustrates one embodiment of a catheter pump configured for percutaneous application and operation.
Figure 2:
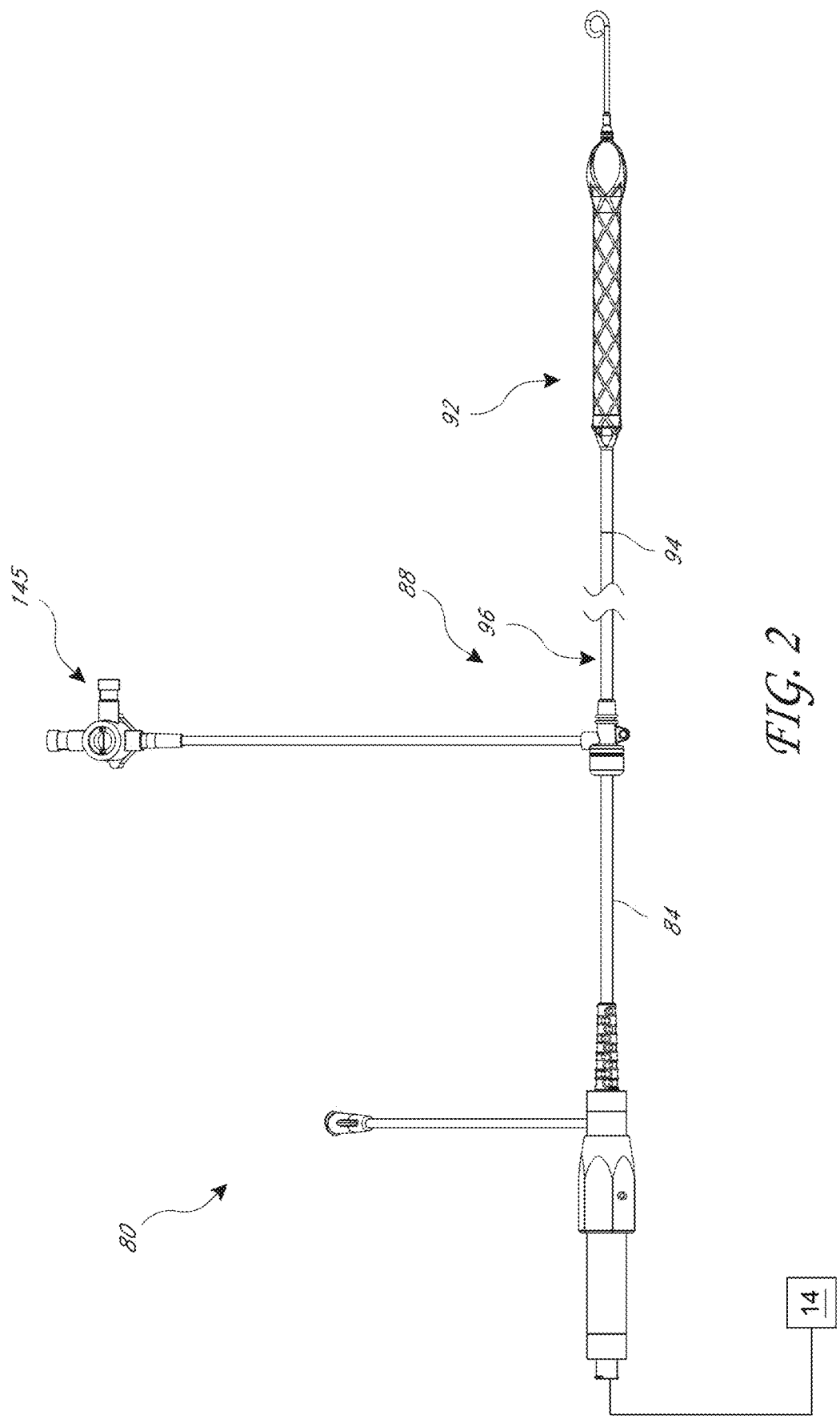
FIG. 2 is a plan view of one embodiment of a catheter adapted to be used with the catheter pump of FIG. 1.
Figure 3:
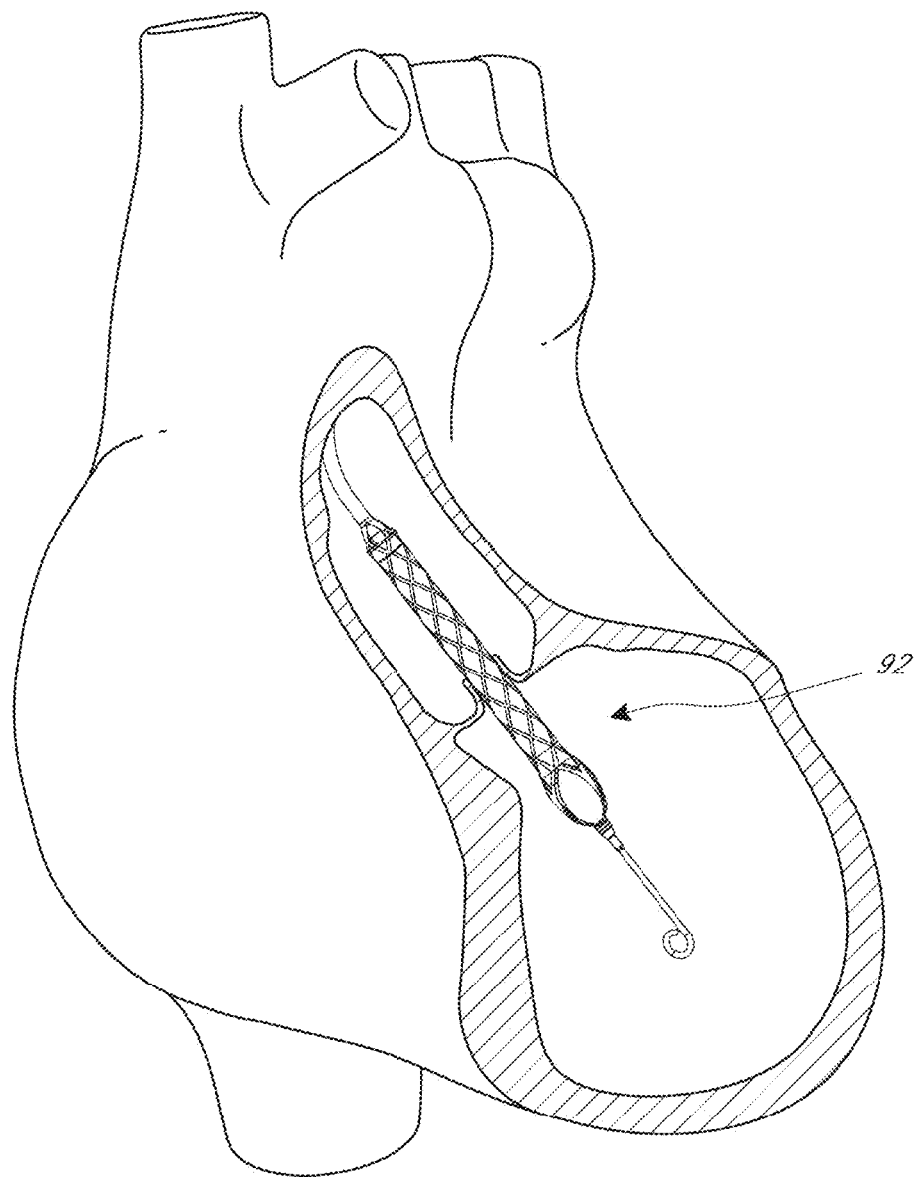
FIG. 3 show a distal portion of the catheter system similar to that of FIG. 2 in position within the anatomy.

FIGS. 1-3 show aspects of a catheter pump 10 that can provide high performance including flow rates similar to full cardiac output. The pump 10 includes a motor driven by a controller 22. The controller 22 directs the operation of the motor 14 and an infusion system 26 that supplies a flow of infusate in the pump 10. A catheter system 80 that can be coupled with the motor 14 houses an impeller within a distal portion thereof. In various embodiments, the impeller is rotated remotely by the motor 14 when the pump 10 is operating. For example, the motor 14 can be is disposed outside the patient. In some embodiments, the motor 14 is separate from the controller 22, e.g., to be placed closer to the patient. In other embodiments, the motor 14 is part of the controller 22. In still other embodiments, the motor is miniaturized to be insertable into the patient. Such embodiments allow the drive shaft to be much shorter, e.g., shorter than the distance from the aortic valve to the aortic arch (about 5 mm or less). Some examples of miniaturized motors catheter pumps and related components and methods are discussed in U.S. Pat. Nos. 5,964,694; 6,007,478; 6,178, 922; 6,176,848; and all of which are hereby incorporated by reference herein in their entirety for all purposes.

FIG. 3 illustrates one use of the catheter pump 10. A distal portion of the pump 10 is placed in the left ventricle LV of the heart to pump blood from the LV into the aorta. The pump 10 can be used in this way to treat patients with a wide range of conditions, including cardiogenic shock, myocardial infarction, and acutely decompensated heart failure, and also to support a patient during a procedure such as percutaneous coronary intervention. One convenient manner of placement of the distal portion of the pump 10 in the heart is by percutaneous access and delivery using the Seldinger technique or other methods familiar to cardiologists. These approaches enable the pump 10 to be used in emergency medicine, a catheter lab and in other non-surgical settings.

FIG. 2 shows features that facilitate small blood vessel percutaneous delivery and high performance up to and in some cases exceeding normal cardiac output in all phases of the cardiac cycle. In particular, the catheter system 80 includes a catheter body 84 and a sheath assembly 88. An impeller assembly 92 is coupled with the distal end of the catheter body 84. The impeller assembly 92 is expandable and collapsible. In the collapsed state, the distal end of the catheter system 80 can be advanced to the heart. In the expanded state the impeller assembly 92 is able to pump blood at high flow rates. FIGS. 2 and 3 illustrate the expanded state. The collapsed state can be provided by advancing a distal end 94 of an elongate body 96 distally over the impeller assembly 92 to cause the impeller assembly 92 to collapse. This provides an outer profile throughout the catheter assembly 80 that is of small diameter, for example 12.5 French as discussed further below.

In some embodiments, the impeller assembly 92 includes a self-expanding material that facilitates expansion. The catheter body 84 on the other hand preferably is a polymeric body that has high flexibility. When the impeller assembly 92 is collapsed, as discussed above, high forces are applied to the impeller assembly 92. These forces are concentrated at a connection zone, where the impeller assembly 92 and the catheter body 84 are coupled together. These high forces, if not carefully managed can result in damage to the catheter assembly 80 and in some cases render the impeller within the impeller assembly 92 inoperable. A reliable mechanical interface is provided to assure high performance. While this interface is extremely beneficial for an assembly with an expandable impeller disposed in an expandable cannula, it also applies to assemblies including a fixed diameter impeller, which may be disposed in an expandable cannula or even in a non-expandable portion in fluid communication with an expandable cannula. In one variation, the impeller is disposed proximal of an expandable cannula in a rigid segment (e.g., a pump ring) and an expandable cannula is provided. The mechanical interfaces and inner and outer sheath assemblies facilitate the collapse of the cannula in such embodiments. A further design permits the impeller to be withdrawn into a rigid structure, e.g., a pump ring, to collapse the impeller before the cannula is collapsed.

The mechanical components rotatably supporting the impeller within the impeller assembly 92 permit high rotational speeds while controlling heat and particle generation that can come with high speeds. The impeller may be rotated as speeds above 6000 RPM, above 9000 RPM, above 10,000 RPM, above 15,000 RPM, above 20,000 RPM, above 25,000 RPM, or above 30,000 RPM. The infusion system 26 delivers a cooling and lubricating solution to the distal portion of the catheter system 100 for these purposes. However, the space for delivery of this fluid is extremely limited. Some of the space is also used for return of the infusate. Providing secure connection and reliable routing of infusate into and out of the catheter assembly 80 is critical and challenging in view of the small profile of the catheter body 84.

Various aspects of the pump and associated components are similar to those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, this application incorporates by reference in its entirety and for all purposes the subject matter disclosed in each of the following concurrently filed applications: application Ser. No. 13/802,556, entitled "DISTAL BEARING SUPPORT," filed on Mar. 13, 2013; application Ser. No. 61/780,656, entitled "FLUID HANDLING SYSTEM," filed on Mar. 13, 2013; application Ser. No. 13/802,570, entitled "IMPELLER FOR CATHETER PUMP," filed on Mar. 13, 2013; application Ser. No. 13/801,528, entitled "CATHETER PUMP," filed on Mar. 13, 2013; and application Ser. No. 13/802,468, entitled "MOTOR ASSEMBLY FOR CATHETER PUMP," filed on Mar. 13, 2013.

Figure 4:
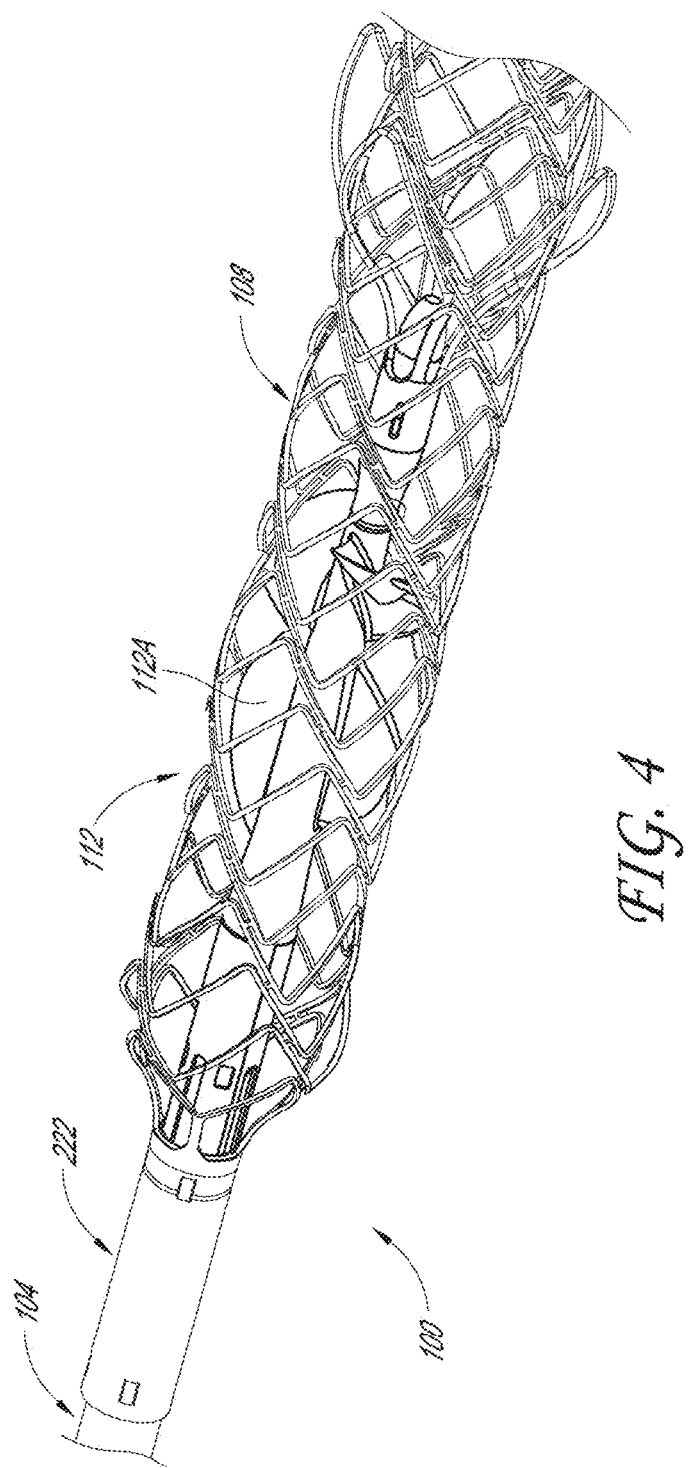
FIG. 4 is a perspective view of a distal portion of a catheter assembly according to one embodiment.
Figure 5:
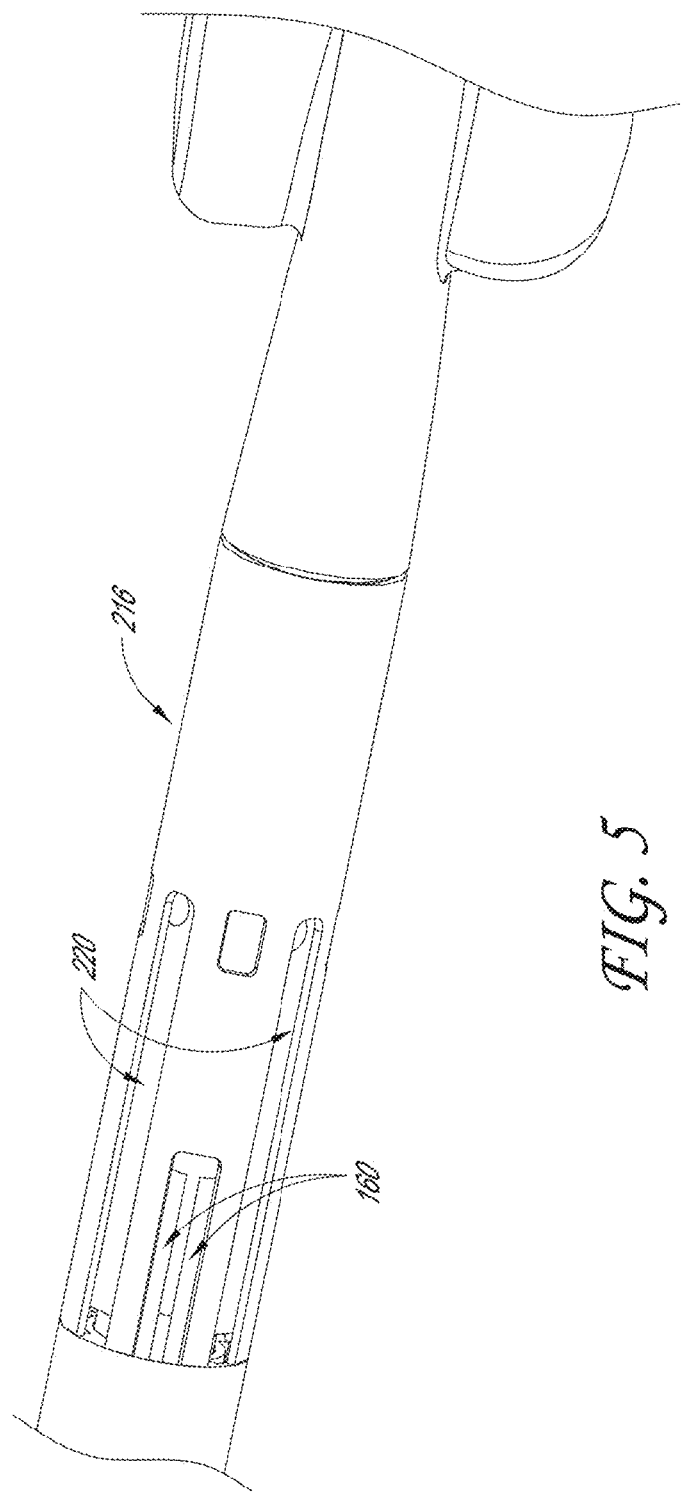
FIG. 5 is a perspective partial assembly detail view of a portion of the catheter assembly of FIG. 4.
Figure 6:
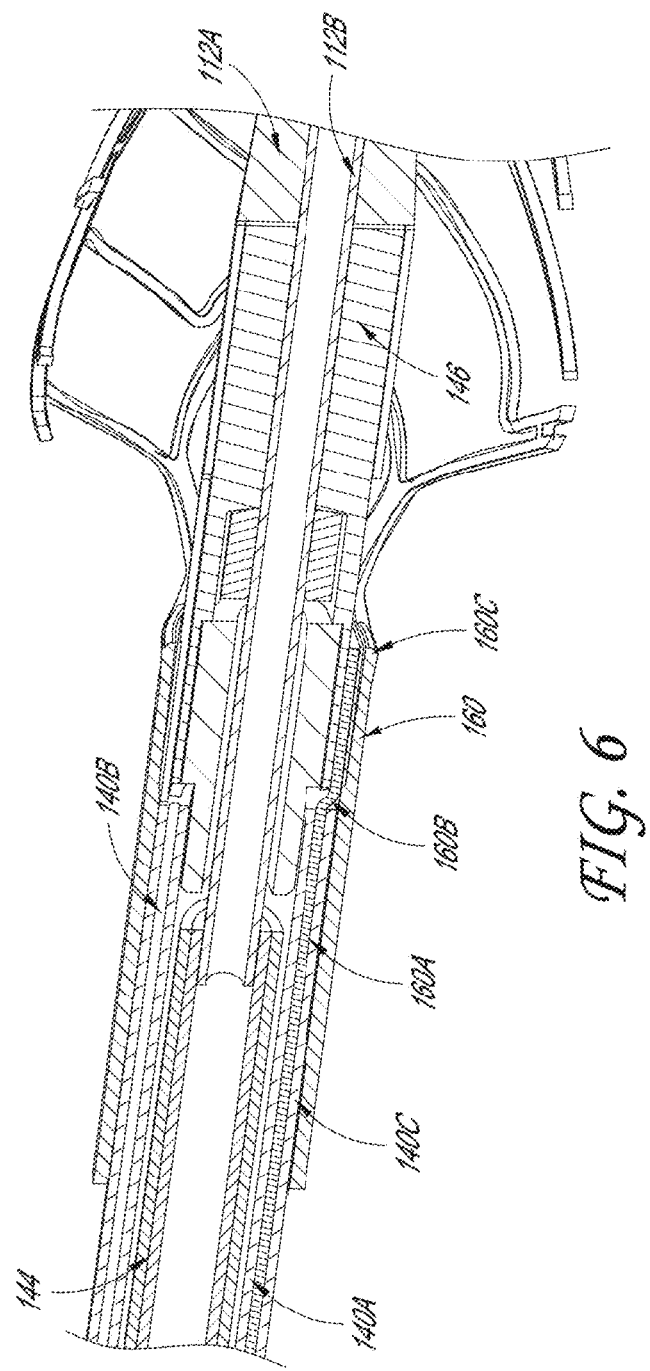
FIG. 6 is a cross-sectional view of a portion of a connection zone of the catheter assembly of FIG. 4.

FIGS. 4-6 show a first embodiment of a working end of a catheter assembly 100 forming a part of one embodiment of the catheter pump 10. The catheter assembly 100 is similar to the catheter system 84 except as discussed differently below. The catheter assembly 100 includes an elongate catheter body 104. A proximal end of the catheter body 104 can be coupled with a motor housing. A distal portion of the catheter body 104 is coupled to a cannula 108 configured to house a high flow rate impeller 112. The exemplary catheter pump can be configured to produce an average flow rate of 4 liters/minute or more at physiologic conditions, e.g., at the typical systolic pressure of a patient needing treatment, such as 60 mmHg. In various embodiments, the pump can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate at 60 mmHg of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

In some embodiments both the cannula 108 and the impeller 112 are actuatable from a first configuration for delivery through a patient to a working site to a second configuration for generating high flow at the working site. The first configuration may be a low profile configuration and the second configuration may be an expanded configuration. The low profile configuration preferably enables access via a femoral artery or other peripheral blood vessel without excessive obstruction of blood flow in the vessel, as discussed further below.

The catheter body 104 preferably has a plurality of lumens, including a first lumen 140 adapted for housing a drive shaft 144, a second lumen 140B for conveying a medical fluid distally within the catheter body 104, and a third lumen 140C for anchoring a bearing housing 146 to the catheter body 104. The drive shaft 144 extends proximally within the catheter body 104 from the impeller 112. The drive shaft 144 couples with the motor at the proximal end and with the impeller 112 at the distal end thereof. The drive shaft 144 can be formed with any suitable structure, but should be sufficient flexible to traverse at least from a peripheral (e.g., femoral) artery to a heart chamber, such as the left ventricle, as well as sufficiently durable to rotate at a high speed for several hours, for several days, and in some cases, months. The drive shaft 144 can be coupled with an impeller assembly 112 including an expandable impeller 112A) disposed on a tubular body 112B FIGS. 4 and 6 shows these structures. The impeller 112A preferably includes an elastomeric polymer structure that can be formed as a unitary body. The tubular body 112B can be a metal hypotube. The tubular body 112B can be received in a distal portion of the drive shaft 144.

Any suitable material or combination of materials can be used for the catheter body 104 or catheter bodies 104A and 304 discussed below and provided in some embodiments. In one embodiment, the catheter body 104 has an inner layer 148 surrounding the lumen 140 that comprises high density polyethylene (HDPE). For example, Marlex 4903 HDPE can be disposed about the lumen 140. If a composite structure is used to form the catheter body 104, the inner layer 148 has a thickness that is sufficient to withstand wear caused by interaction with the drive shaft 144, which can be rotated at a very high speed in some applications, for example from 20,000-40,000 revolutions per minute. The inner layer can have a thickness of 0.003 inches.

Figure 10:
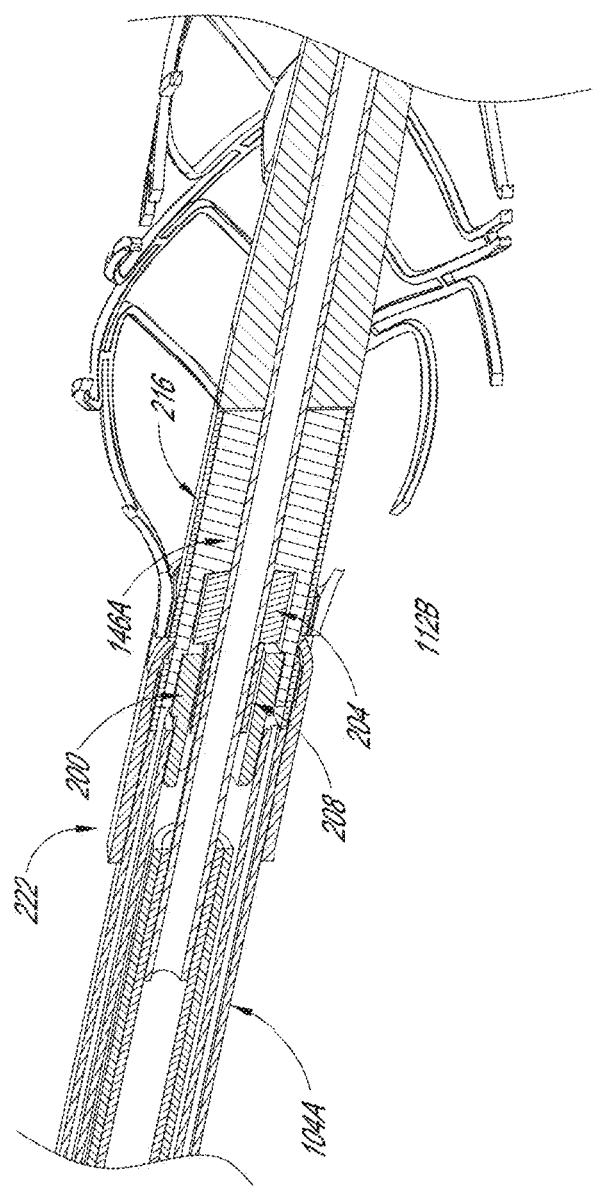
FIG. 10 is a cross-sectional view of a portion of a connection zone of the catheter assembly of FIG. 9.

The second lumen 140B extends from a proximal end in fluid communication with a source of infusate, which can be a medical fluid (e.g., saline), to a distal end adjacent to the impeller assembly 112. For example, the second lumen 140B can have an outlet disposed adjacent to a flow channel formed in or about the bearing housing 146. Examples of bearing housing flow channels are shown in FIGS. 5, 10, and in application Ser. No. 13/343,618, which is hereby incorporated by reference. In one embodiment of the catheter body 104A, the second lumen 140B is generally circumferentially elongated, for example having two sides that are curved with an arc length of about 0.030 inches and two sides that are straight, disposed along a radial direction of the catheter body 104 and about 0.010 inches in length. A proximal end of the second lumen 140B is coupled with a port, which may be similar to the luer 145 in FIG. 2, or other fluid connection device. Any suitable connection between a port and lumen can be used, e.g., a skived connection can be used.

The third lumen 140C can be used to enhance the security of the connection between the catheter body 104, 104A and the bearing housing 146. For example, the third lumen 140C can be sized to receive a plurality of, e.g., two, pull wires 160. The pull wires 160 can take any suitable form, but preferably are sized to be easily received within the lumen 140C. In one embodiment, the lumen 140C is spaced apart from but about the same size as the second lumen 140B and the pull wires are generally rectangular in shape, e.g., having a thickness of about 0.005 inches and a width of about 0.010 inches. The pull wires 160 can be formed of any material that is sufficiently rigid in tension, e.g., of stainless steel with pull strength of at least about 300 ksi. In one arrangement, the pull wires 160 extend at least about three inches into the elongate body 104 in the third lumen 140C and extend out of the third lumen 140C to overlay the bearing housing 146 as shown in FIG. 5.

FIG. 6 shows one approach to compactly arranging the pull wires 160 and structure coupled together thereby. In particular, a proximal portion 160A of the wires is received within a distal length of the third lumen 140C and a distal portion 160C of the wires is disposed distal of the catheter body 104. A transition 160B is provided between the zones 160A, 160C causing the proximal portion 160A to be disposed closer to the longitudinal axis of the impeller catheter assembly 100 than is the distal portion 160C. This permits the outer surface of the catheter body 104 to be closer to the longitudinal axis of the catheter assembly 100 than if the pull wires were straight with the distal portion 160C in the same position as illustrated.

Providing a plurality of pull wires provides redundancy in the connection between the catheter body 104, 104A and the bearing housing 146. In some cases, this redundancy is not needed and a single wire can be used. The redundancy is beneficial, however, because substantial tension force is applied at this connection point when the expandable cannula 108 is collapsed. In one technique relative motion is provided between the catheter body 104, 104A and an outer sheath disposed over the catheter body until the outer sheath slides over a proximal portion of the cannula 108. Further relative motion causes the cannula 108 to be compressed, but not without a substantial force being applied thereto. This force is born at several points, including at the junction between the catheter body 104, 104A and the bearing housing 146. Disconnection of the bearing housing 146 would be problematic, requiring complex procedures to extract the disconnected distal working end of the catheter assembly 100.

Figure 12:
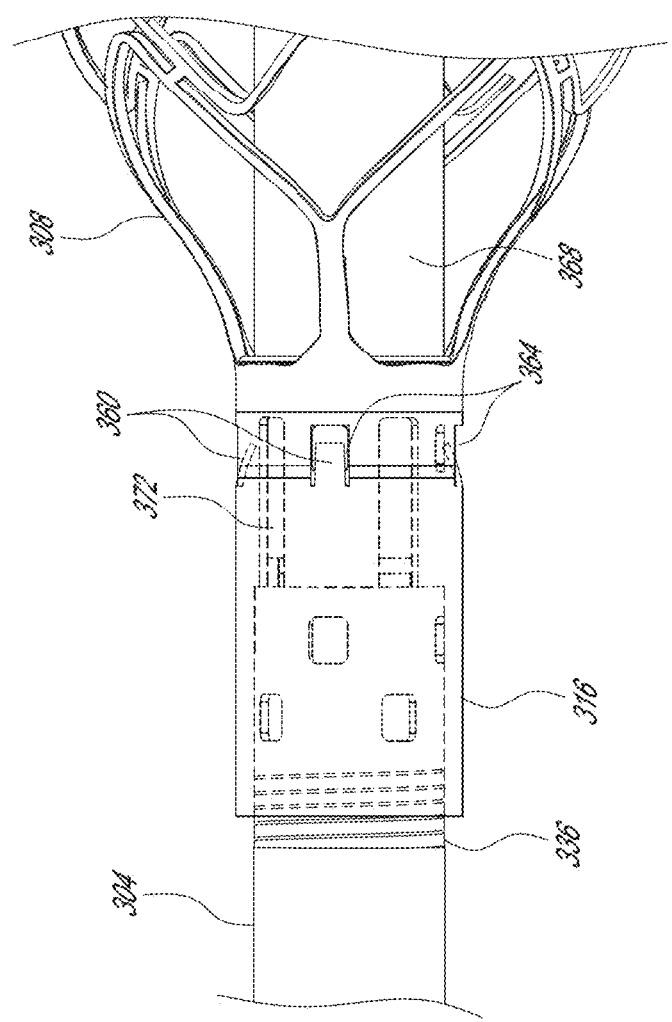
Figure 13:
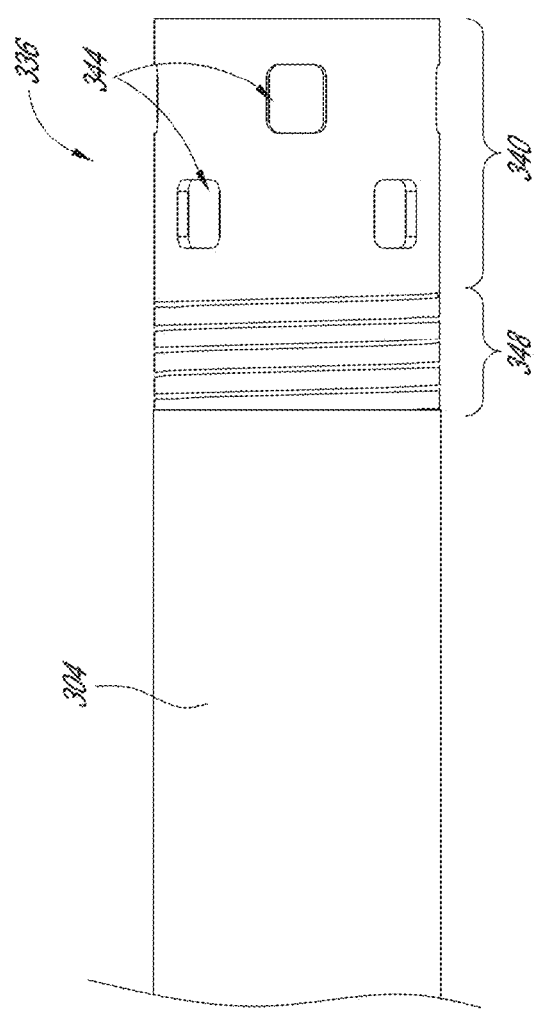
Figure 14:
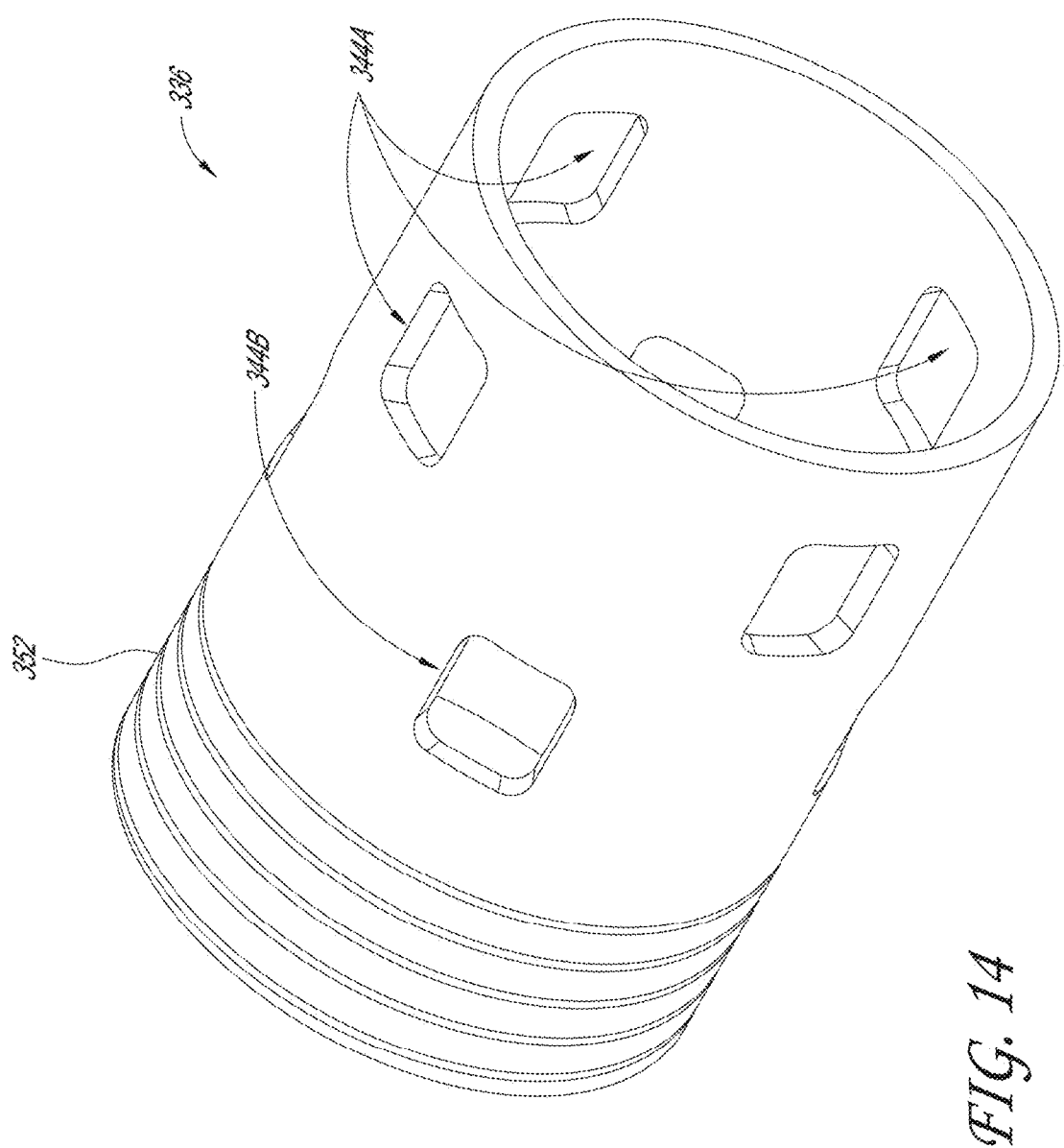

The pull wires 160 preferably are located close together on the same side of the catheter body 104, 104A. This arrangement enhances bending flexibility, which is beneficial if tortuous vasculature must be traversed to deliver the catheter assembly 100 to a treatment site, e.g., a heart chamber. FIGS. 12-14 illustrate other techniques for enhancing the security of the connection of the bearing housing 146 to a catheter body.

In some embodiments, placing a radiopaque marker on a distal portion of the catheter assembly 100 is advantageous to confirm the location of the working end, e.g., of the cannula 108 and/or impeller 112 prior to and/or after deployment.

Gross mechanical properties of the catheter body 104 can be varied along the length thereof to provide appropriate flexibility and maneuverability within the vasculature to facilitate delivery and operation of the catheter pump into which the catheter assembly 100 is incorporated. For example, in one embodiment, the catheter body 104 is stiffest near the distal end where the catheter body 104 is joined to the working end. In one embodiment, a distal section of the catheter body 104 comprises a relatively soft or flexible material, such as Pebax®. Pebax® is a thermoplastic elastomer, such as a polyether block amide, marketed by Arkema of France. In various embodiments, the material has a hardness of about 100 D or less, 75 D or less, 72 D or less, 60 D or less, or 50 D or less. In various embodiments, the material has a flexural modulus of less than about 400 MPa, less than about 300 MPa, less than about 200 MPa, less than about 100 MPa, less than about 50 MPa, or less than about 30 MPa. A proximal section of the catheter body 104 may comprise a material, such as Vestamid®. In various embodiments the material has a hardness greater than about 40 D, greater than about 50 D, greater than about 60 D, or greater than about 72 D. In various embodiments, the material has a tensile strength of about 45 MPa. In various embodiments, the material has a flexural modulus of greater than about 20 MPa, greater than about 40 MPa, greater than about 75 MPa, greater than about 85 MPa, greater than about 120 MPa, greater than about 220 MPa, greater than about 350 MPa, or greater than about 1000 MPa. Vestamid is a thermoplastic elastomer marketed by Evonik Industries® of Germany known to have high elasticity and good recovery. Between these relatively hard sections ends, a middle section of the catheter body comprises a material having a lower hardness. In an exemplary embodiment, the middle section is formed of MX1205 Pebax®. In an exemplary embodiment, the relatively hard sections are formed of Vestamid. The low hardness section provides a softer structure in the vicinity of the aortic arch, where the catheter may be resting on the vessel wall in use. One or more intermediate hardness sections can be provided between the distal, proximal and middle sections. These arrangements are also relevant to the other inner catheter bodies discussed herein, including bodies 104A, 304. In various respects, the hardness of the material refers to the bending or torsional stiffness of the respective material. For example, in various embodiments, the relatively hard sections generally require a meaningfully higher moment before they bend relatively to the relatively softer materials. In various embodiments, the relatively hard section resist deformation in use compared to the relatively soft sections which are configured to deform (e.g. bend).

Alternately, or in addition to these features, the catheter body 104 can have different diameters along its length to provide several important performance benefits. The diameter of a proximal portion of the catheter body 104 can be relatively large to enhance pushability and trackability of the catheter assembly 100. The diameter of a distal portion of the catheter body 104 can be relatively small to enhance flexibility of the distal tip and also to match the profile of the bearing housing 146 such that the lumens 140B align with flow channels at least partly defined by the bearing housing (e.g., the slots 220 discussed below). The enlarged diameter and enhanced hardness at the proximal end both contribute to the maneuverability of the catheter assembly 100. These arrangements are also relevant to the other inner catheter bodies discussed herein, including bodies 104A, 304 and the catheter assemblies 100A, 300, and 400 (discussed below).

Figure 9:
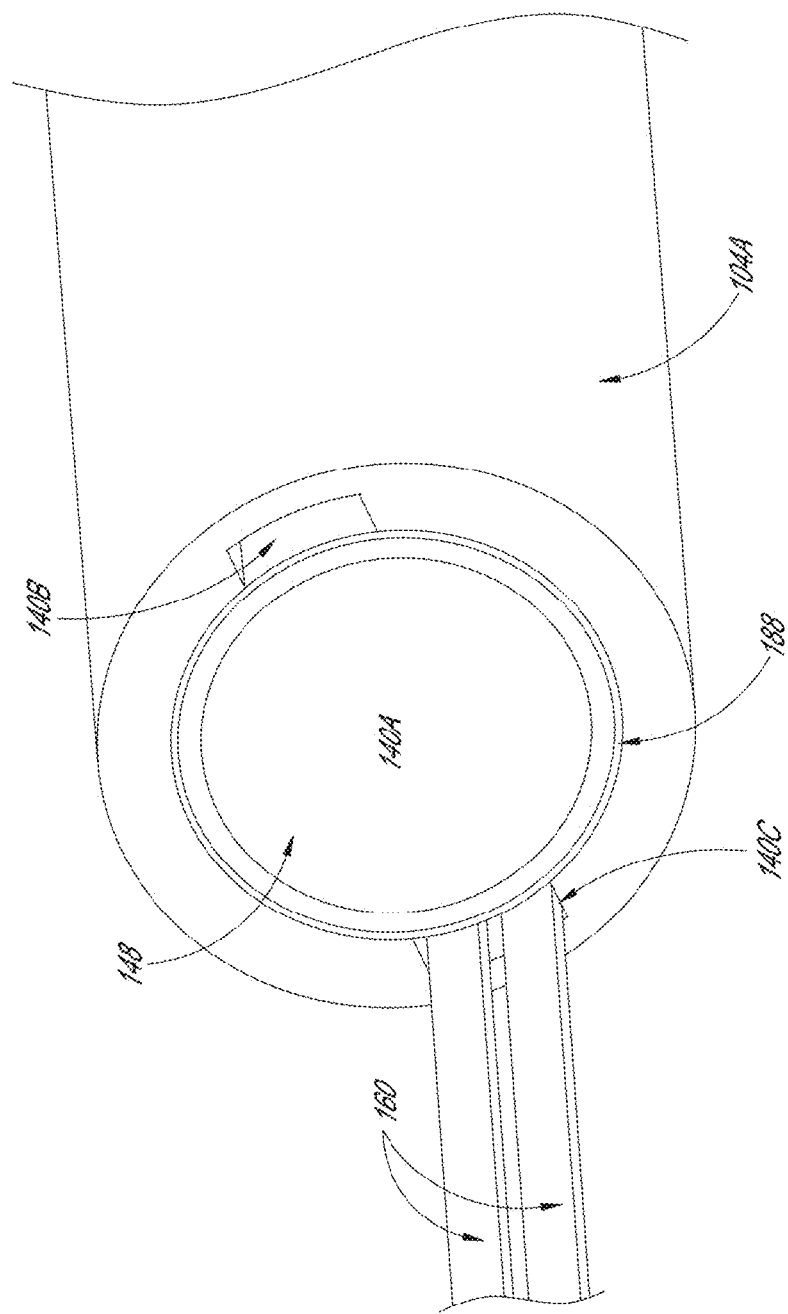
FIG. 9 is a detail view of a mechanical interface of a catheter assembly.

In addition to the foregoing structures for varying the stiffness along the length of the catheter body 104, a separate stiffening component, such as a braid 188, can be disposed in the catheter body 104, 104A. In one embodiment, a 0.001 inch by 0.003 inch flat wire of 304V stainless steel is embedded in the catheter body 104, 104A and the braid includes a 70 ppi configuration. The braid 188 can be positioned in any suitable location, e.g., between an inner layer 148 and an outer layer, as shown in FIG. 9 of the drawings.

As discussed above, the catheter assembly 100 preferably also includes an outer sheath or sheath assembly 88 provided over the elongate body 104, 104A to aid in delivering, deploying and/or removing the impeller 112. The outer sheath 88 can include an elongate body 96 (see FIG. 2) comprising an inner surface surrounding a lumen disposed therein. The inner lumen can comprise a low friction material or layer. For example, a thickness of PTFE can be provided adjacent the inner lumen. In one embodiment, one or more separate materials can be provided at an outer surface of the elongate body 96.

The elongate body 96 preferably is connected at the proximal end with a proximal hub and/or a suitable connector, such as a Tuohy Borst connector. The proximal hub can include a luer fitting.

Figure 6A:
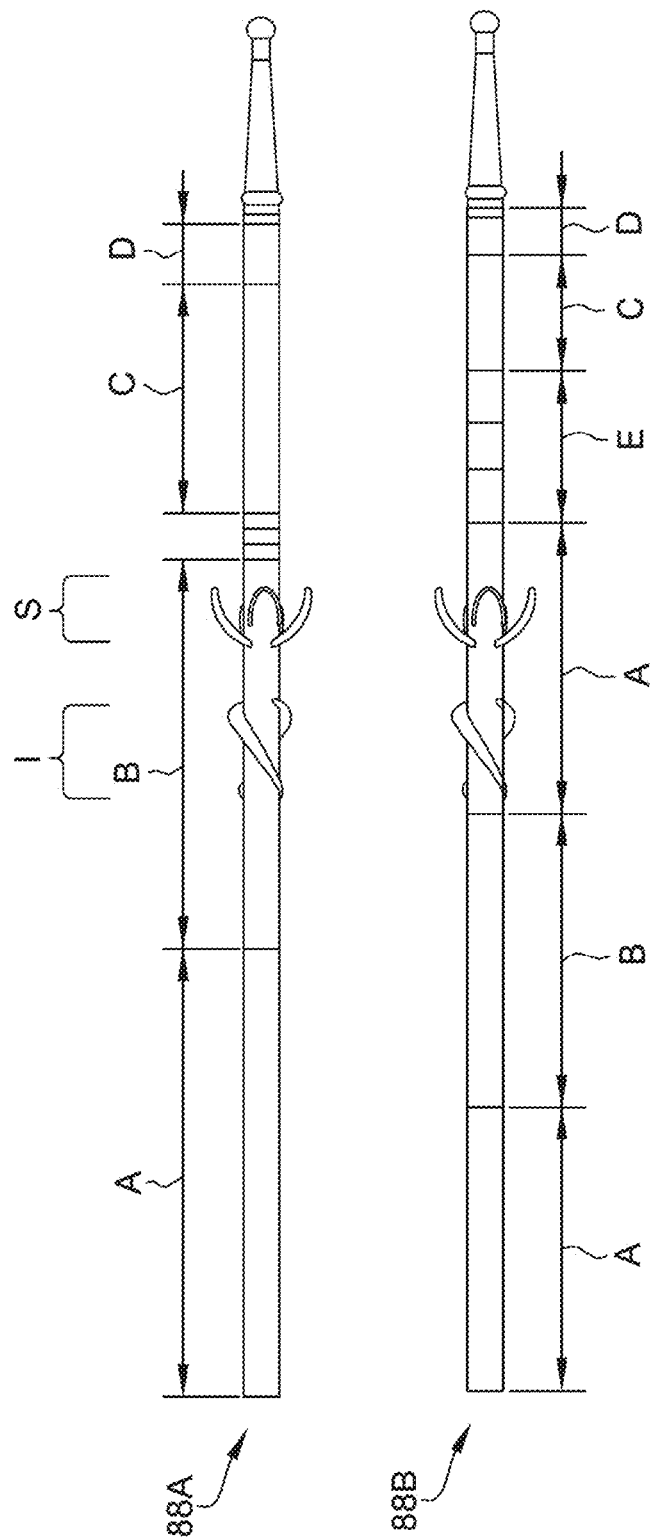
FIG. 6A is a schematic view of embodiments of an outer sheath configured to enhanced delivery and retrieval performance.

The outer sheath 88 also may have varied hardness or other gross mechanical properties along its length to provide appropriate flexibility and maneuverability within the vasculature to facilitate delivery and operation of the catheter pump into which the outer sheath is incorporated, and also to facilitate collapse of the cannula 108 after deployment thereof. FIG. 6A illustrates schematically bulk property variation in two embodiments of the sheath assembly 88. In particular, an elongate body extending between the proximal and distal ends of the sheath assembly 88 has different hardness at different locations along the length. The different hardnesses enhance the maneuverability of the sheath assemblies 88A, 88B to minimize kinking of the elongate body as the catheter assembly 100 is tracking toward the heart and/or when the elongate body is used to collapse an expandable cannula or impeller, as discussed elsewhere herein.

The elongate body of the sheath assembly 88A has a proximal portion "A" with a highest hardness. The proximal portion A can comprise vestamid or other similar material. A portion "B" distal of the proximal portion A and residing over a zone of the cannula in which the impeller I and the distal bearing support S (if present) are housed can have a hardness that is lower than that of the portion A. Portion B can comprise 55 D pebax. In some embodiments, as discussed further below a segment of portion B can act as a radiopaque marker for the sheath during delivery and/or removal of the catheter pump from the patient. A portion "C" disposed distal of the portion B can comprise a material with the lowest hardness of the elongate body of the sheath assembly 88A, e.g., can comprise MX1205. A portion "D" at the distal end of the elongate body of the sheath assembly 88A can have a relatively high hardness, e.g., 72 D pebax. The sheath assembly 88A upon distal movement over the expanded cannula initially contacts the cannula with the relatively hard material of portion D. The relatively soft portion C may contact the vasculature as the catheter assembly 100 is advanced, and its relatively soft structure is biocompatible. Portion B has a hardness that is high enough to protect the zones I and S of the cannula, impeller, and support. Portion A is the hardest of the materials used in the sheath assembly 88A, to aid in maneuverability.

The elongate body of the sheath assembly 88B has a proximal portion and distal bearing zone portion "A" with a highest hardness. The proximal portion A can comprise vestamid or other similar material. A portion "B" between the proximal portion A and the distal bearing zone portion A. The portion B resides adjacent to the transition from the catheter body 104 to the cannula proximal portion 116 and can have a hardness that is lower than that of the portion A. Portion B can comprise 55 D pebax. Portions C and D in the sheath assembly 88B are the same as in the sheath assembly 88A. A portion E is disposed between the portions A and C, e.g., distal of the portion A disposed over the distal bearing support. Portion E can include a series of progressively softer lengths, e.g., a first length of 72 D pebax, a second length of 63 D pebax, and a third length of 55 D pebax. Other materials and hardnesses can be used that provide good resistance to kinking in the delivery of the catheter assembly 100 and/or in the process of re-sheathing the expanded cannula and impeller.

Figure 6B:
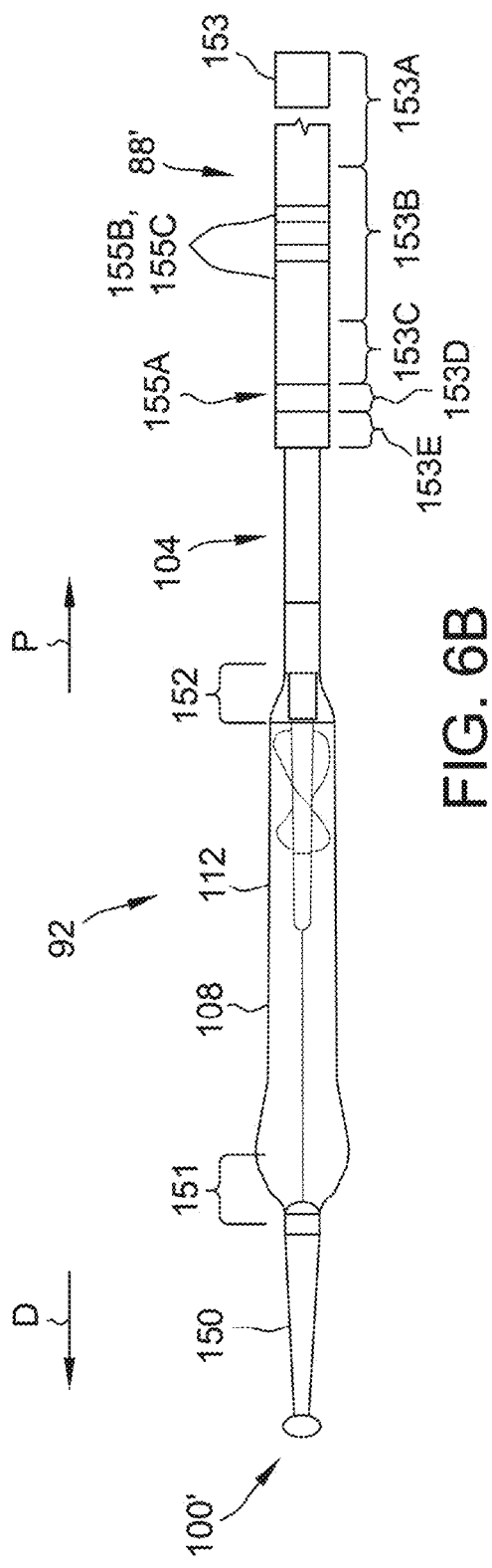
FIG. 6B is a schematic side view of a distal portion of a catheter assembly, in accordance with various embodiments.

FIG. 6B is a schematic side view of a distal portion of a catheter assembly 100', in accordance with various embodiments. As with the embodiments described above, the catheter assembly 100' can comprise an impeller assembly 92 having an impeller 112 disposed inside an expandable and collapsible cannula 108. An inlet 151 and an outlet 152 can be defined in the cannula 108, such that during operation of the catheter assembly 100', the impeller 112 draws blood into the cannula 108 by way of the inlet 151 and expels blood out of the cannula 108 by way of the outlet 152. An atraumatic tip 150 can be disposed distal the cannula 108, and can be configured to provide an atraumatic contact interface when the tip 150 contacts the anatomy. As explained above, a sheath assembly 88' can be disposed about a catheter body 104, within which are provided one or more supply and waste lumens and a drive shaft that imparts rotation to the impeller 112.

Figure 6C:
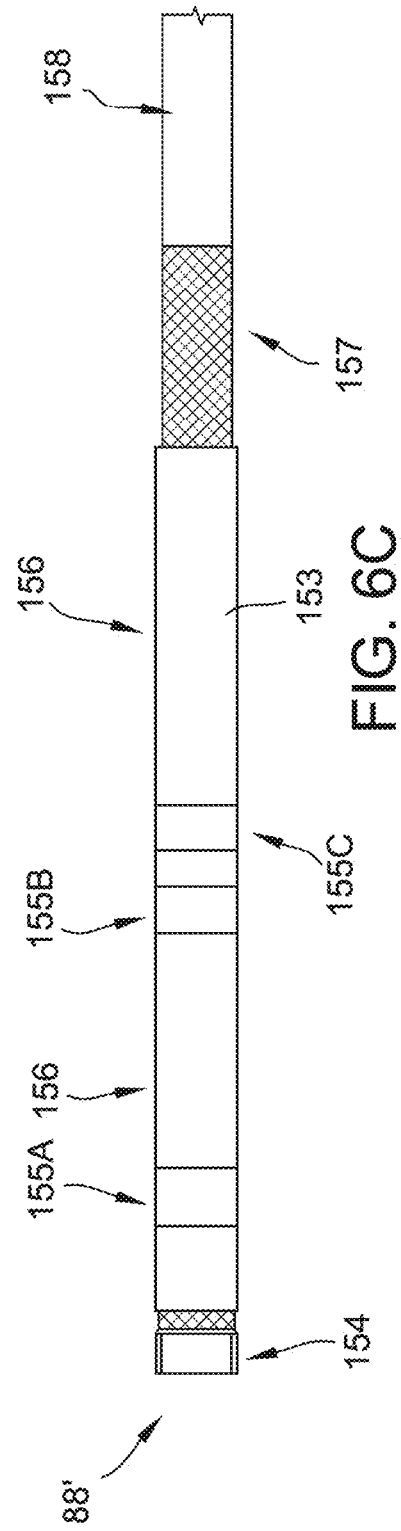
FIG. 6C is an enlarged view of the sheath assembly shown in FIG. 6B.

FIG. 6C is an enlarged view of the sheath assembly 88' shown in FIG. 6B. The sheath assembly 88 can comprise a catheter body having an internal lumen. As shown in FIGS. 6B and 6C, and as explained herein, the sheath assembly 88' can be translated proximally P relative to the impeller assembly 92 to expose the impeller assembly 92. As the impeller assembly 92 is exposed from the proximally sliding sheath assembly 88' (or by relative motion between the sheath assembly 88' and the impeller assembly 92 including by advancing the catheter body 104 relative to the sheath assembly 88'), the impeller 110 and the cannula 108 can self-expand into a deployed configuration. The pump, of which the catheter assembly 100' is a part, can be activated to pump blood through the cannula 108. In the deployed configuration, the pump can provide improved flow rates and patient outcomes as compared with non-expandable and other smaller diameter catheter pumps. After the procedure, the sheath assembly 88 can be moved distally D relative to the impeller assembly 92 to contact the cannula 108 and cause the cannula 108 and impeller 110 to move to a stored configuration. Relative motion between the sheath assembly 88' and the impeller assembly 92 including by retracting the impeller assembly 92 into the sheath assembly 88' can also be provided. Once stored, the impeller assembly 92 and sheath assembly 88 can be withdrawn from the anatomy.

The sheath assembly 88' can include a sheath body 153 that defines an interior lumen in which the impeller assembly 92 is stored during insertion and/or removal of the catheter assembly 100' from the anatomy. As shown in FIG. 6C, the sheath body 153 can comprise a multi-layered structure of different materials. For example, an inner liner 158 can be provided to enable reduced friction during use. For example, the liner 158 can comprise a material with a low co-efficient of friction, such as one or more of a suitable polymer, such as polytetrafluoroethylene (PTFE). The sheath assembly 88' can comprise an outer jacket 156 disposed about the inner liner 158. The inner liner 158 can have a wall thickness sufficiently small so as to enable flexibility during use. The wall thickness of the inner liner 158 can be in a range of 0.001 inches to 0.005 inches, in a range of 0.001 inches to 0.004 inches, or in a range of 0.001 inches to 0.002 inches, e.g., about 0.0017 inches.

As explained above with respect to FIG. 6A, the outer jacket 156 can be formed of a plurality of materials having different stiffnesses (e.g., varying along a length of the sheath assembly 88') and/or elasticities to reduce kinking during use of the catheter assembly 100. For example, the outer jacket 156 can comprise one or more of MX1205, Pebax 55 D, Pebax 72 D, and Vestamid. In one embodiment Vestamid is provided in a proximal portion 153A that extends from a proximal end of the outer jacket 156 to a location adjacent to the distal end. The proximal portion 153A has stiffness configured for advancing the catheter assembly 100' to the heart by way of the aorta. A braided structure 157 can be provided along at least a portion of the length of the sheath assembly 88' to provide reinforced mechanical strength, e.g., improved longitudinal or axial strength and improved radial strength. In one embodiment a stiffness contribution by the braided structure 157 varies along the length of the sheath assembly 88', for example providing a denser braid in the proximal portion 153A than in portions of the sheath assembly 88' distal the proximal portion 153A. The braided structure 157 can be provided radially between the outer jacket 156 and the inner liner 158 in various embodiments. In various other embodiments, the braided structure 157 can be integrated or embedded within the outer jacket 156 or within the inner liner 158. The braided structure 157 can comprise a matrix or mesh of metallic material that is shaped in a tubular profile. In various embodiments, the braided structure 157 can comprise stainless steel, for example stainless steel 304V full hardness. The inner diameter of the sheath body 153 can be in a range of 0.1 inches to 0.2 inches, e.g., in a range of 0.155 inches to 0.17 inches (for example, about 0.163 inches). The outer diameter of the sheath body 153 can be in a range of 0.14 inches to 0.25 inches, or in a range of 0.16 inches to 0.21 inches, e.g., about 0.186 inches. A length of the sheath body 153 can be in a range of 90 cm to 110 cm, or in a range of 100 cm to 105 cm, e.g., about 102.5 cm+/−0.3 cm.

The sheath assembly can include a distal tip 154 at the distalmost end of the sheath assembly 88', such that the distal tip 154 contacts the proximal portion of the cannula 108 (e.g., contacts the cannula mesh at or near the outlet 152) when the sheath assembly 88' is urged distally D to collapse the impeller assembly 92. Beneficially, the distal tip 154 can comprise a material that is suitably flexible so as to expand outwardly to accommodate forces imparted on the tip 154 by the wall of the cannula 108. For example, when the distal tip 154 is urged distally D over the cannula 108, the cannula 108 may impart radially outward forces to the distal tip 154. The tip 154 can be sufficiently flexible as to accommodate the radially outward forces without excessively yielding or breaking, but may be sufficiently stiff so as to ensure collapse of the cannula 108. For example, the distal tip 154 can expand radially outward to receive the cannula 108, and portions of the jacket 158 directly proximal the tip 154 may provide a stiffer collapsing portion so as to cause the cannula 108 and impeller 112 to collapse into the sheath assembly 88'. In various embodiments, the distal tip 154 can be made of an elastic polymer, such as PTFE. In other embodiments, the distal tip can include a combination of materials including PEBAX. In one arrangement, a PEBAX cylindrical member is joined to a proximal portion of a distal-most portion 153E by a folded over zone of the liner 158. In other words, the liner 158 can be disposed on the inside of the sheath assembly 88' and a length of the liner can be folded over and around the PEBAX cylindrical member such that the end of the liner 158 can be disposed proximal of the distal end of and around radially outward of the inside lumen of the sheath assembly 88'. In some embodiments, the outer diameter of the distal tip 154 can be slightly smaller than the outer diameter of the sheath body 153. The outer diameter of the distal tip 154 can be in a range of 0.14 inches to 0.25 inches, or in a range of 0.16 inches to 0.21 inches, for example about 0.1895 inches.

In addition, the sheath assembly 88' can comprise one or more position markers 155a, 155b, 155c that are configured to indicate to the clinician the position and/or orientation of the impeller assembly 92. A second portion 153B of the sheath body 153 disposed distal the proximal zone 153A can extend from proximal of the markers 155b, 155c to distal thereof. The second portion 153B can be configured with less stiffness than the proximal portion 153A. The second portion 153B can have a portion of the braided structure 157 that is less stiff, e.g., lower braid density, than the portion of the braided structure 157 in the proximal portion 153A. The second portion 153B can comprise a material that is less stiff than the material in the proximal portion 153A. The second portion 153B can be formed of 55 D PEBAX. FIG. 6B shows that the second portion 153B can span the location of the markers 155b, 155c. A third portion 153C disposed distal the second portion 153B can have a lesser stiffness than in the second portion 153B. Any technique for providing a less stiff configuration in the third portion 153C can be provided as discussed above. The third portion 153C can extend from the second portion to a proximal end of the marker 155a. A fourth portion 153D can correspond to the marker 155A. The fourth portion 153D can have any suitable configuration. In one embodiment, the fourth portion 153D is stiffer than the third portion 153C. In one embodiment, the fourth portion 153D has the same stiffness as the second portion 153B.

The position markers 155a-155c can comprise radiopaque markers that are visible to the clinician using, for example, an x-ray fluoroscope. The position markers 155a-155c can comprise a Pebax 55 D material with a radiopaque component, such as 60% tungsten. The distal-most marker 155a can be used during delivery of the catheter assembly 100 to provide the clinician with an estimated real-time position of the distal portion of the catheter assembly 100 as the catheter assembly 100 is inserted into, or removed from, the anatomy of the patient. For example, the clinician can view the distal-most marker 155a in real-time on a display device to guide the catheter assembly 100 to the treatment location. The middle marker 155b and the proximal marker 155c can be used to position the catheter assembly 100 relative to the treatment region to provide accurate of the catheter assembly 100 prior to unsheathing the cannula 108. For example, in some embodiments, the clinician can view the middle and proximal markers 155b, 155c to ensure that the markers 155b, 155c are near (e.g., are straddling) the aortic valve before initiation of a left ventricular assist procedure.

Figures 1, 6D:
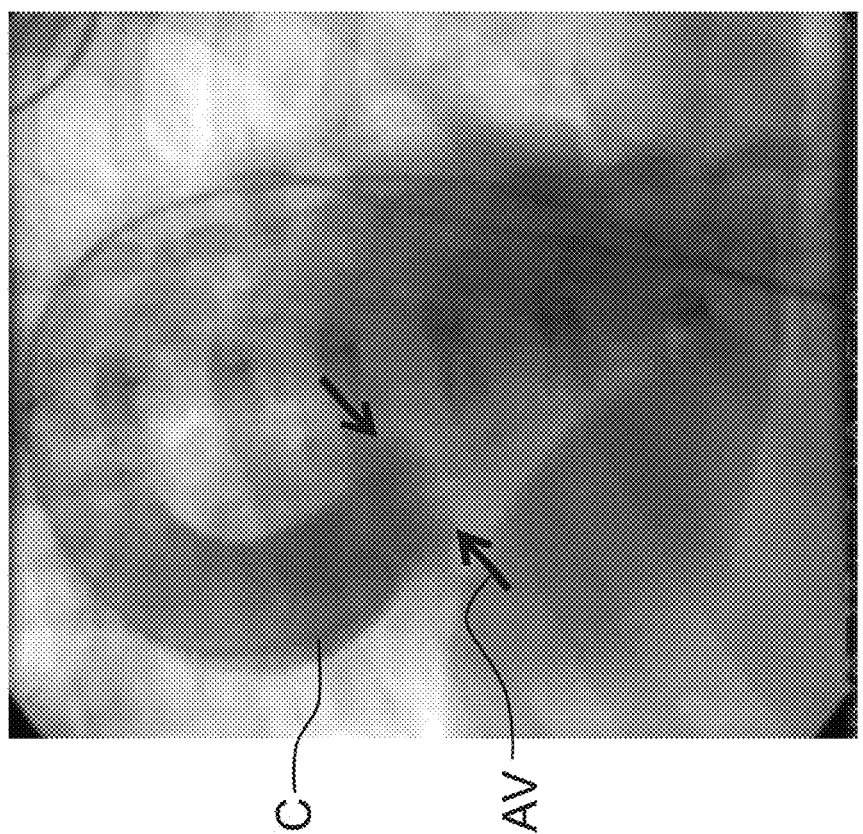
Figures 2, 6D:
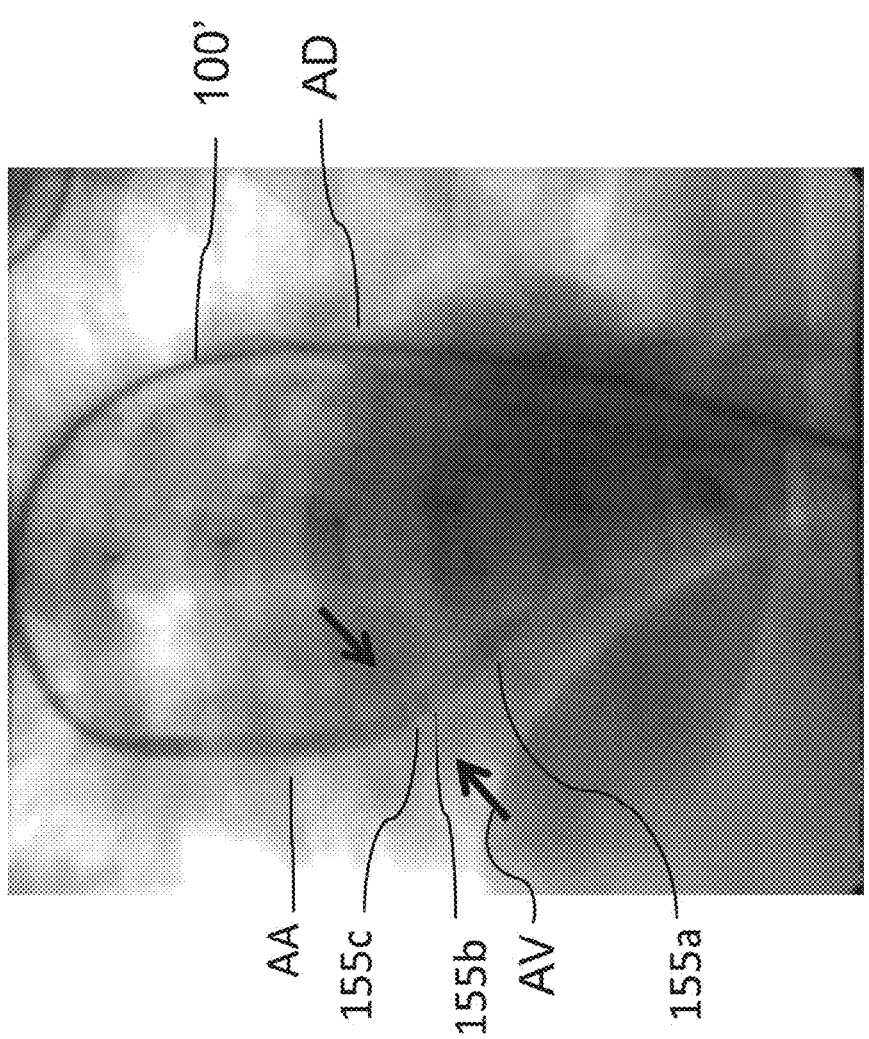
Figures 3, 6D:
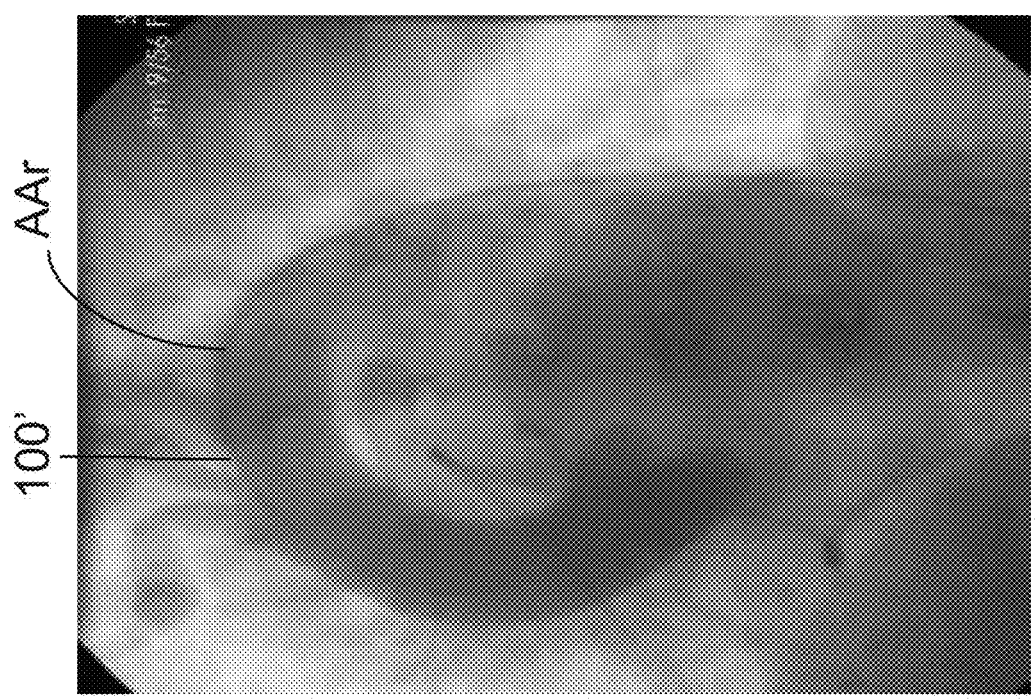
Figures 4, 6D:
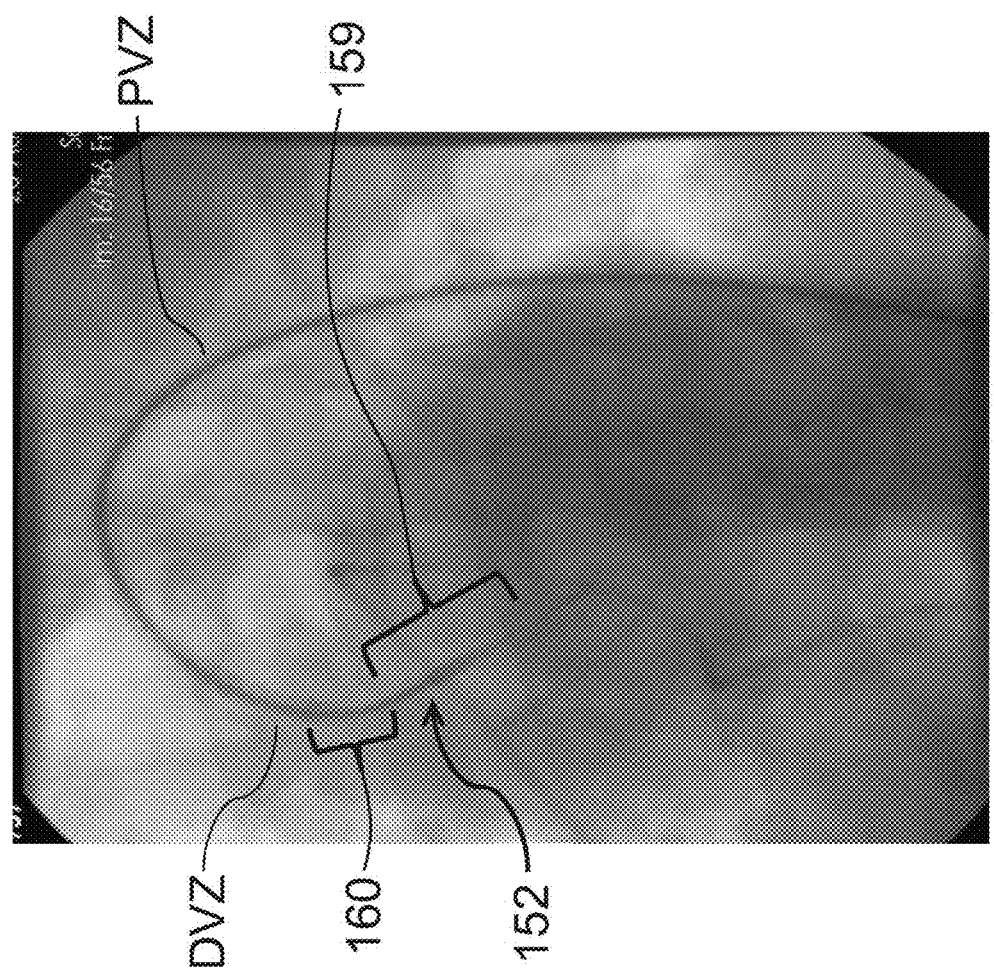
Figures 5, 6D:
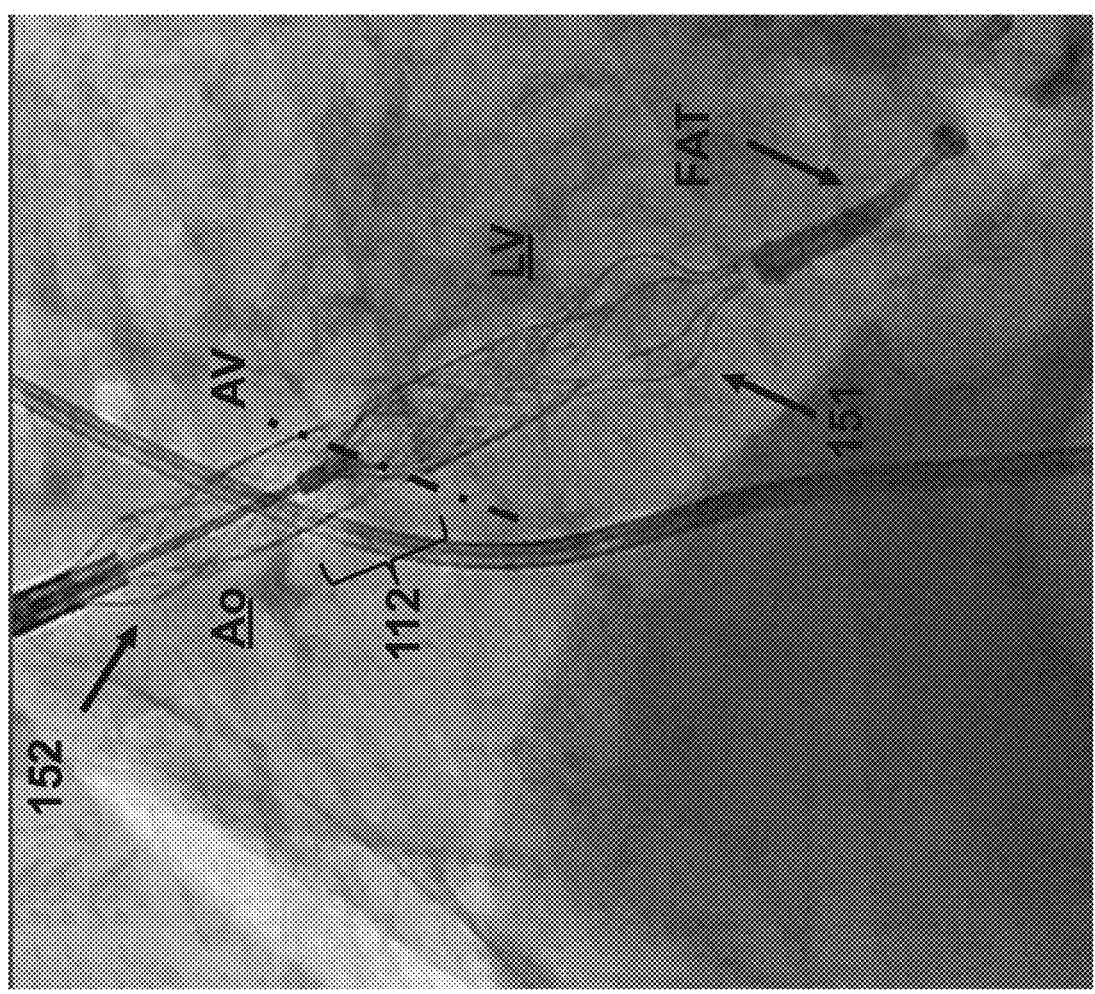

FIG. 6D-1 to 6D-5 are fluoroscopic views of an example method for deploying the catheter assembly 100' in connection with operating a pump. In FIG. 6D-1 a catheter C is positioned on the aorta side of the aortic valve and contrast is injected into the aorta to identify the location of the aortic valve AV. FIG. 6D-2 shows that hereafter, the catheter assembly 100' is advanced into the patient, up the descending aorta AD, down the ascending aorta AA and into the heart across the aortic valve AV. In one technique, the position of the marker 155a can be confirmed to be in the left ventricle. The position of the proximal two marker bands 155b, 155c can be confirmed to be at the aortic valve AV. In one technique, the band 155b can be distal the valve AV and the band 155c can be proximal the valve. The band 155a can be disposed over the inlet 151 and the bands 155b, 155c can be at or distal to the outlet 152.

FIG. 6D-3 shows that after the catheter assembly 100' is positioned across the aortic valve AV and when so positioned, the catheter assembly 100' follows the outer radius of the aortic arch AAr.

FIG. 6D-4 shows that following the deployment of the catheter assembly 100' across the ventricle, the catheter assembly 100' provides for proper positioning and orienting across the aortic valve. For example, it may be desired to provide a substantially straight segment 159 from proximal to the outlets 152, through the aortic valve AV and into the ventricle. The straight segment 159 can include the location of the impeller 112 in one embodiment. The straight segment 159 can extend proximally and distally of the impeller 112 in one embodiment. In one approach, the configuration of the catheter assembly 100' provides that a bending zone or bending section 160 is disposed proximal of the straight segment 159. The bending zone 160 can be disposed distally of a distal vascular contact zone DVZ. The distal vascular contact zone DVZ can correspond to where an outside surface of the sheath body 153 contacts the wall of the ascending aorta. The vascular contact zone DVZ is located at or between the junction between the ascending aorta and the aortic arch such that the straight segment 159 is not required to bend to reach the aortic valve AV.

Further stability of the catheter assembly 100' can be provided by a technique in which a proximal vessel contact zone PVZ is provided. The proximal vessel contact zone PVZ can be located at or distal the junction of the aortic arch and the descending aorta. The catheter assembly 100' is configured by the stiffness and/or the resilience of the components thereof to generate a restoring force. The restoring force can arise due to stiffness of, the elasticity of, or the stiffness and the elasticity of the catheter assembly 100' when the curved shaped is formed when the normally straight catheter assembly 100' is deployed around the outer radius of the aortic arch. The restoring force can act on the walls of the aorta to provide an additional stabilizing force to help retain the catheter assembly 100' in place around the outer radius of the aortic arch. This force combined with focusing the flex point between the distal contact zone DVZ and the outlet 152 provide greater stability of the working elements and outflow of the catheter pump.

As shown in FIG. 6D-5, for left ventricular assist procedures, the impeller assembly 92 can be positioned so that it straddles the aortic valve AV, with the inlet 151 disposed in the left ventricle LV and the outlet 152 disposed in the aorta Ao. The impeller assembly 92 can be activated to pump blood proximally from the left ventricle LV through the inlets 151 and into the cannula 108. Blood can be ejected through the outlet 152 and into the aorta Ao. During pumping, it can be important to maintain the impeller assembly 92 at a relatively stable position relative to the aorta 192 and aortic valve 190. Stability can be provided by the structures and techniques discussed above. Stable positioning can have a number of benefits including maintaining the pumping effectiveness of the catheter pump. Stability can reduce uncontrolled and repeated impact on the walls of the aorta in the aortic arch. Stability can reduce or eliminate the motion of the distal portion of the catheter assembly 100' within the anatomy. Furthermore, the position of the inlet 151 and outlet 152 straddling the aortic valve AV can be maintained. That is, if the distal portion of the catheter assembly 100' is mobile within the anatomy, there is a risk that both the inlet 151 and the outlet 152 will be in the aorta during some or all of the operation of the pump or the inlet 151 and the outlet 152 will be in the left ventricle LV during some or all of the operation of the pump. These conditions can prevent direct pumping from the heart and reduce the effectiveness of the heart pump.

Beneficially, the outer sheath assembly 88' disclosed herein can have a variable stiffness along its length, as explained herein, which can enable the sheath assembly 88' to bear gently but consistently against one or both of the proximal contact zone PVZ and the distal contact zone DVZ during operation of the catheter pump. In contrast, conventional catheter based heart pump devices are much more flexible and move cyclically from the outer radius of the aortic arch to the inner radius thereof, and then back to the outer radius. Advantageously, the sheath assembly 88' can contact one or both of the distal and proximal contact zones DVZ, PVZ to maintain the position of the impeller assembly 92 during operation. This improvement over conventional catheter based heart pump helps to maintain stable relative position of these components, e.g., providing a more consistent tip-gap between an outer tip of the blades of the impeller 112 and the inner wall of the cannula 108. This improvement over conventional catheter based heart pump devices also provides more consistent and predictable interaction between the atraumatic tip 150 and the inner walls of the ventricle to reduce any adverse side effects of disposing the distal portion of the catheter assembly 100' within the left ventricle.

Figure 7:
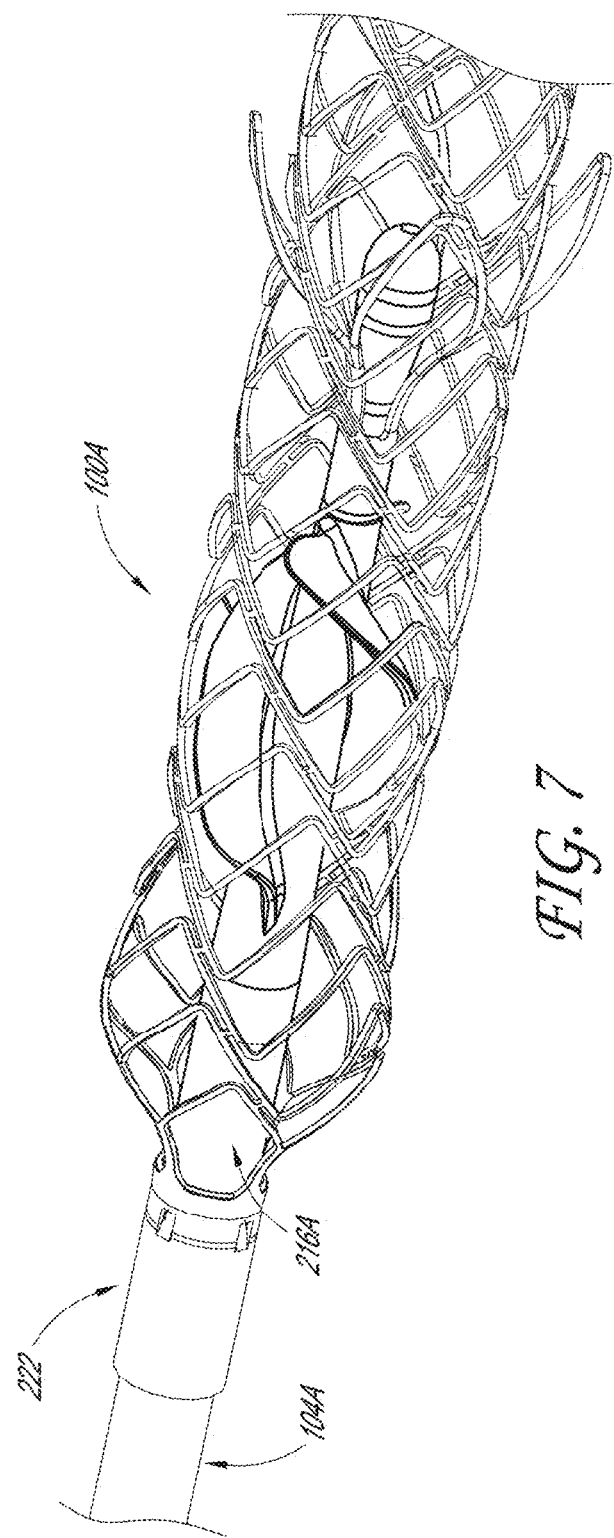
FIG. 7 is a perspective view of a distal portion of a catheter assembly according to another embodiment.

FIGS. 7-10 incorporate the discussion above and illustrate additional features and embodiments. FIGS. 7 and 9 illustrate aspects of a mechanical interface between a bearing housing 146A and the catheter body 104A. In particular, a coupler 200 is provided between the bearing housing 146A and the catheter body 104A. The coupler 200 (also shown in FIG. 6) is similar to the coupler 628 disclosed in U.S. application Ser. No. 13/343,618, which is hereby incorporated by reference herein. In this configuration a thrust bearing 204 is provided in the bearing housing 146A. In some embodiments, a thrust bearing brace 208 is disposed just proximal of the thrust bearing 204. The thrust bearing brace 208 can take any suitable form, but preferably provides a shoulder or other radial protrusion from the outer surface to the impeller shaft 112B that abuts a proximal face of the thrust bearing 204. The thrust bearing brace 208 minimizes or completely prevents movement of the thrust bearing 204 on the impeller shaft 112B. Such movement is possible because the impeller on the impeller shaft 112B generates significant distally oriented thrust. In some assemblies, the thrust bearing 204 is interference fit onto the impeller shaft 112B. When sized and fit properly, this connection maintains the relative position of thrust bearing 204 to the impeller shaft 112B under the thrust forces that are applied. The thrust bearing brace 208 provides redundancy of this connection. In one embodiment, the thrust bearing brace 208 comprises a short hypotube that is coupled with, e.g., laser welded to the impeller shaft 112B. The weld completely prevents relative axial movement between the impeller shaft 112B and the thrust bearing brace 208. The abutment between the trust bearing 204 and the thrust bearing brace 208 prevent relative movement between the thrust bearing 204 and impeller shaft 112B if the coupling between the impeller shaft 112B and the thrust bearing 204 loosens.

Figure 8:
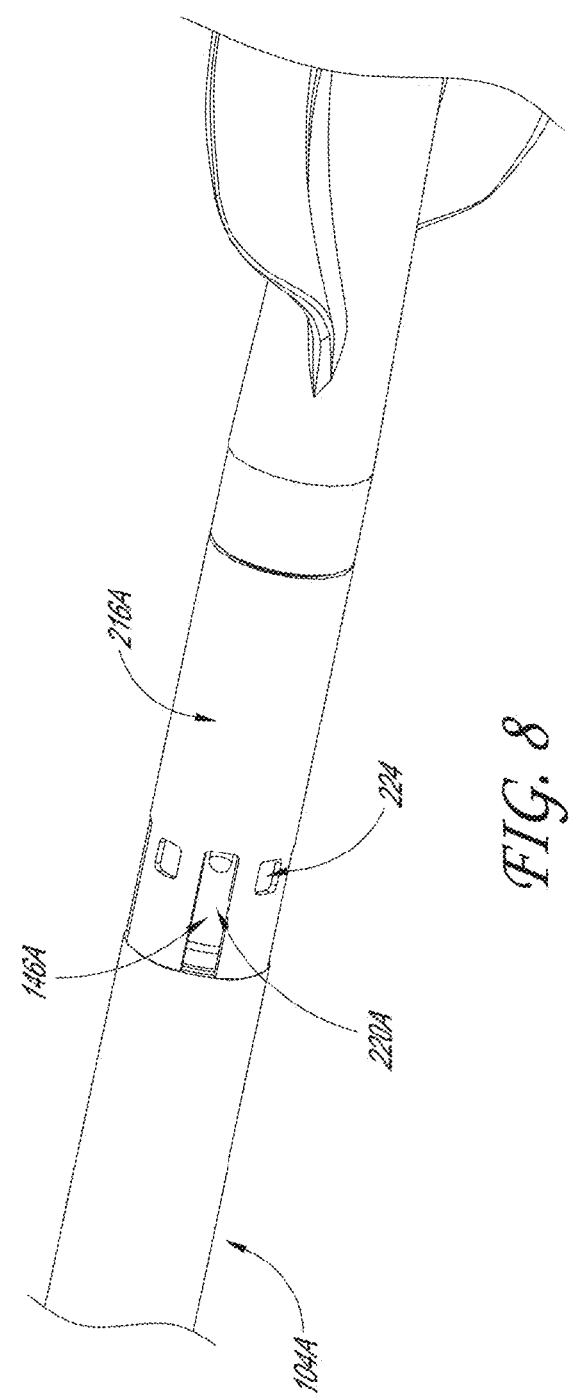
FIG. 8 is a perspective partial assembly detail view of a portion of the catheter assembly of FIG. 7.

FIG. 8 shows that an outer surface of the bearing housing 146A can be covered by a cylindrical sleeve 216. The sleeve has at least one slot 220 formed therein. The slot 220 can be circumferentially aligned to or otherwise in fluid communication with the second lumen 140B such that infusate fluid flowing distally in the lumen enters the slot and can be directed distally in a space formed between the bearing housing 146A, the sleeve 216 and an outer sleeve, that may be a proximal portion 222 of the frame-like structure of the cannula 108. This structure is shown in FIGS. 4 and 5. In FIG. 4, the cannula 108 is displaced proximally to reveal the sleeve 216, which would be covered by a proximal cylindrical portion 222 of the cannula 108 when the catheter assembly 100 is assembled. A difference between the impeller assembly/catheter body interface of the embodiment of FIGS. 4-6 and the embodiment of FIGS. 7-11 is that the sleeve 216A includes recess 220A in fluid communication with the lumen 140B. The recesses 220A are fluid flow structures. Other ports into the inside of the bearing housing 146A can be accessed through apertures 224 that do not extend to the proximal end of the sleeve 216. The apertures are fluid communication structures through which fluid can flow into the bearing housing. Flow from the lumen 104B to the apertures 224 can be provided through a circumferential space defined between the outer surface of the sleeve 216 and an inner surface of the proximal portion 222 of the cannula 108. See FIG. 10. In some cases, the apertures 224 are additionally or alternately adapted to receive components of secondary mechanical interface discussed below. In other embodiments, troughs are formed in an outer surface of the bearing housing are enclosed by the inner surface of the sleeve 216 to form enclosed flow channels for infusate.

Catheter pumps incorporating the catheter assembly and variation thereof can be configured to deliver average flow rates of over 4 liters/minute for a treatment period. For example, a treatment period can be up to 10 days for acute needs, such as patient in cardiogenic shock. Catheter pumps incorporating the catheter assembly 100 or such modifications thereof can be used for shorter periods as well, e.g., for support during high risk catheter or surgical procedures.

Also, catheter pumps incorporating the catheter assembly 100 or modifications thereof can be used for left or right side heart support. Example modifications that could be used for right side support include providing delivery features and/or shaping a distal portion that is to be placed through at least one heart valve from the venous side, such as is discussed in U.S. Pat. Nos. 6,544,216; 7,070,555; and US 2012-0203056A1, all of which are hereby incorporated by reference herein in their entirety for all purposes. For example, the catheter assembly 100 or modifications thereof can be configured to be collapsed to be deliverable through a 13 French introducer sheath and can be expanded to up to 24 French when deployed. In one embodiment, the outer profile of the catheter assembly 100 or modifications thereof is approximately 12 French, but can be any size that is insertable into a femoral artery without requiring surgical cutdown. The catheter assembly 100 can be as large as 12.5 F to be inserted through a 13 French introducer sheath. One method involves deployment of the cannula 108, having an expandable nitinol structure, across the aortic valve. In this position, the impeller 112 can be disposed on the aorta side of the valve and a distal length of the cannula 108 within the ventricle.

In other embodiments, the outer profile of the catheter assembly 100 or modifications thereof is less than 12 French, e.g., about 10 French. The 10 French configuration can be useful for patients with lower flow needs, e.g., about 3 liters per minute or less at physiologic conditions. In another example, an 8 French configuration can be useful for patients with lower flow needs, e.g., about 2 liters per minute or less at physiologic conditions.

Figure 11:
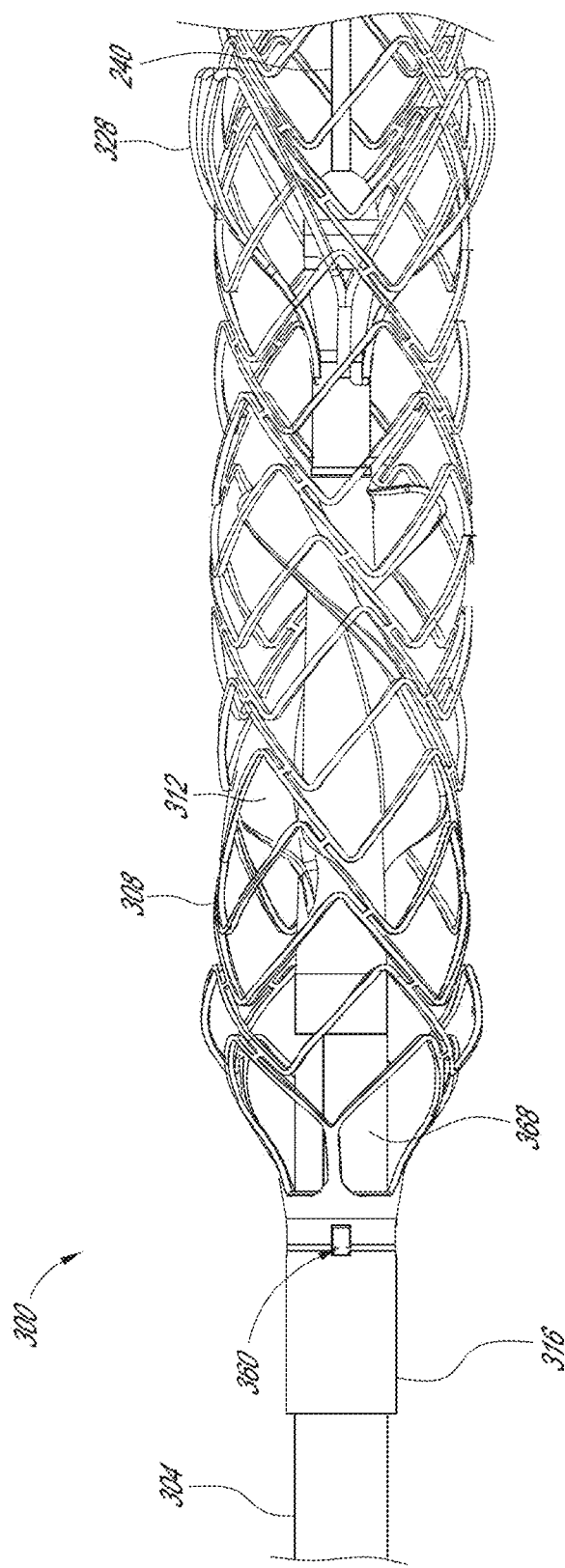
FIGS. 11-14 illustrate features of additional embodiments of catheter assemblies having robust mechanical interface.

FIGS. 11-14 illustrate additional embodiments in which the structural integrity of a catheter assembly 300 is enhanced to provide security in connection with sheathing an expandable portion. FIG. 11 shows that a distal portion of the catheter assembly 300 includes components similar to those hereinbefore described. In particular, the catheter assembly 300 includes a catheter body 304, an expandable cannula 308 and an expandable impeller 312. The catheter body can take any suitable form. In one embodiment, the catheter body 304 has variable hardness along its length.

The cannula 308 includes a self-expanding structure enclosed in a polymeric film. The self-expanding structure can be a distal portion of a member having a non-expanding tubular portion 316 proximal of the self-expanding structure. The tubular portion 316 plays a role in anchoring the cannula 308 to the catheter body 304.

FIG. 11 shows that a support member 328 can be positioned within the cannula 308 to prevent unacceptable variance in the gap between the tip of the impeller 312 and the inside surface of the cannula. More details of this structure are set forth in concurrently filed application Ser. No. 13/802,556, entitled "DISTAL BEARING SUPPORT," filed on Mar. 13, 2013, which is incorporated hereby by reference herein for all purposes. Successful collapse of the cannula 308, the impeller 312, and the support 328 focuses forces on a joint between the cannula 308 and the catheter body 304.

FIGS. 11-14 illustrate features that enhance the security of the connection catheter body 304 and the cannula 308. In FIG. 11, no separate structure is shown between the catheter body 034 and the non-expanding tubular portion 316. These structures are joined in other manners, such as indirectly by the force transfer capability of the pull wires discussed above and/or by an adhesive. In FIG. 12, the distal end of the catheter body 304 is coupled with a ferrule 336. The ferrule 336 is an example of a structure to mechanically join the catheter body 304 to the cannula 308. In one embodiment, the ferrule 336 includes a distal zone 340 for mechanically joining the ferrule 336 to the catheter body 304. The distal zone 340 is also configured to mechanically couple with the cannula 308, for example by welding. A plurality of apertures 344 is provided in one embodiment for mechanically joining the ferrule 336 to the catheter body 304. The apertures 344 enable the material of the catheter body 304 to extend into the distal zone 340. In one technique the ferrule 336 is disposed over the catheter body 304 which extends into the apertures 344.

The apertures 344 can be arranged in multiple zones. In one embodiment a first zone is disposed distally of the second zone. The first zone can be disposed adjacent to the distal end of the ferrule 336 and the second zone is disposed proximal of the first zone. The first zone can include four apertures 344A spaced evenly about the periphery of the body of the ferrule. The second zone can include a plurality of (e.g., four) apertures 344B spaced evenly about the periphery of the body of the ferrule 336. A specific advantageous embodiment provides four apertures 344B in the second zone. The apertures 344B of the second zone can be spaced evenly about the body of the ferrule 336. Preferably the apertures 344 of the first and second zones are offset to provide a great deal of redundancy in the security of the connection of the catheter body 304 to the ferrule 336. For example, the apertures 344 in the first and second zones can be offset by one-half the circumferential distance between adjacent apertures 344.

The ferrule 336 also includes a proximal zone 348 disposed proximally of the aperture 344. The proximal zone 348 preferably is configured to provide an excellent fluid seal between the ferrule and the non-expandable tubular portion 316 of the cannula 308. In one embodiment, the proximal zone 348 includes a plurality of recesses 352 in the outer surface of the proximal portion 348. The recesses 352 can take any form consistent with good sealing, and in one embodiment the recesses are turns of a continuous helical groove in the outer surface of the ferrule 336. The helical groove is configured to receive a sealant that can bridge from the base of the grooves to the inner surface of the proximal portion 316 of the cannula 308. In one embodiment, the sealant includes an adhesive that can flow into the helical groove and be adhered to the inner surface of the proximal portion 316 of the cannula 308.

Although the weld and adhesive that can be formed or disposed between the ferrule 336 and the proximal portion 316 of the cannula 308 can provide excellent security between these components of the catheter assembly 300, a supplemental securement device 360 can be provided in some embodiments. FIG. 11 illustrates one embodiment in which a mechanical securement device 360 is provided. The mechanical securement device 360 includes a cantilevered member that can be deformed from the non-expandable proximal portion 316 of the cannula 308 into corresponding recesses disposed inward of the securement device.

In one embodiment, a recess 364 is provided within the catheter assembly 300 to receive the securement device 360. The recesses 364 can be formed in an internal structure disposed within the proximal portion 316. In a first variation, a sleeve 368 is provided immediately within the non-expandable proximal portion 316 of the cannula 308. The sleeve 368 is provided and fills the volume between a bearing housing 372 and the proximal portion 316. The bearing housing 372 facilitates rotation of the impeller shaft and the flow of infusate. The sleeve 368 has slots and/or other fluid communication structures formed therein that direct flow from channels in the catheter body 308 to flow channels in the bearing housing 372. In one embodiment, the sleeve 368 has a plurality of small apertures that are disposed between flow slots. The apertures and slots can be similar is shape and form to the apertures 224 and slots 220 discussed above.

In other embodiment, apertures can be formed in the bearing housing 372. For example, the bearing housing 372 can have a plurality of channels aligned with flow passages in the catheter body 304. In such embodiment, apertures for receiving the securement device 360 can be provided directly in the bearing housing 372. In another variation, apertures are provided that extend through the sleeve 368 and into the bearing housing 372.

Modifications of catheter pumps incorporating the catheter assembly 300 can be used for right side support. For example, the elongate body 304 can be formed to have a deployed shape corresponding to the shape of the vasculature traversed between a peripheral vascular access point and the right ventricle.

Any suitable manufacturing method can be used to cause a portion of the catheter body 304 to be disposed in the apertures 344. For example, in one the catheter body 304 and the cannula 308 are to be joined. The cannula 308 has the tubular portion 316 which is to be disposed over the catheter body 304. The ferrule 336 is a metallic body that is an important part of one form of a mechanical interface. The ferrule 336 has an inner surface and apertures 344 that act as a first interface zone and an outer surface that acts as a second interface zone. The ferrule 336 is positioned such that the inner surface is disposed over the outer surface of short length of the catheter body 304 adjacent to the distal end thereof.

In one technique, the outer surface of the catheter body 304 is mechanically coupled to the ferrule 336 by a process that involves heating. The distal portion of the catheter body 304 and the ferrule 336 are heated sufficiently to cause at least a portion of the catheter body to transition to a state with low resistance to deformation. The low resistance state can be a fluid state or just a state in which the material of the catheter body 304 if more malleable. In the state having low resistance to deformation, the catheter body 304 flows through or protrudes into the apertures 344. Because the material is formed continuously from a location inside the inner surface of the ferrule to outside the inner surface, a strong mechanical coupling is provided between these components.

The tubular portion 316 of the cannula 308 can be coupled with the ferrule 336 by any suitable technique. In one embodiment, the tubular portion 316 and the ferrule 336 are indirectly coupled through sleeve 368 discussed more below. In particular, the distal end of the ferrule 336 can be welded to the proximal end of the sleeve 368 and a second connection can be provided between the portion 316 and the sleeve as discussed elsewhere herein. In another embodiment, the ferrule 336 can be directly connected by a suitable technique, such as welding if suitable materials are provided. These structures are also illustrated in FIG. 16 below, which shows further details of the connection by the ferrule 336.

The foregoing technique of heating the catheter body 304 to cause the material thereof to be coupled with the proximal portion 160A of the pull wire(s) 160. Another technique for joining the pull wires 160 to the catheter body 304 is by an epoxy or other adhesive at the proximal end of the wires and/or catheter body 304. A distal section of the pull wires 160 within the catheter body 304 can be left un-adhered to the catheter body, such that this section of the pull wires 160 can move relative to the catheter body or "float" to enhance flexibility of the distal portion of the catheter body in some embodiments. The proximal portion 160A provides a first interface zone of a mechanical interface between the catheter body 104 and the bearing housing 146. The distal portion 160C provides a second interface zone that can be coupled with the bearing housing 146 by a suitable technique, such as welding. In another embodiment, the sleeve 216, 216A is formed of a material to which the pull wires can be welded or otherwise mechanically secured.

FIG. 11 illustrates an additional optional feature that can facilitate treatment with a catheter pump including the catheter assemblies disclosed herein or any of the pumps discussed in U.S. application Ser. No. 13/343,618 and Ser. No. 13/343,617, which are hereby incorporated herein by reference. A deployment system is provided by combining the catheter assembly 300 (or any other discussed or claimed herein) with a guide wire guide 240. The guide wire guide 240 can be configured as a small elongate tubular member sized to be advanced in a lumen formed in the drive shaft 144. The guide wire guide 240 includes a lumen that is sized to receive a guidewire (not shown). The wall thickness of the guide wire guide 240 is thin enough to fit within the allotted tolerance for tracking the catheter assemblies discussed herein through the vasculature. The guide wire guide 240 wall thickness is also thin enough to permit the guide wire guide 240 to be withdrawn from between the guide wire and the catheter assembly once the guidewire is in place without damaging either of these structures or disrupting the position of guidewire excessively. In various embodiments, the guide wire guide 240 includes a self-healing member that remains within the catheter assembly when the tubular portion is removed. The self-healing member has an end wall that re-seals when the guidewire is removed. Thus, the guide wire guide 240 facilitates loading the catheter assemblies onto a guidewire for a percutaneous delivery within a patient.

Figure 15:
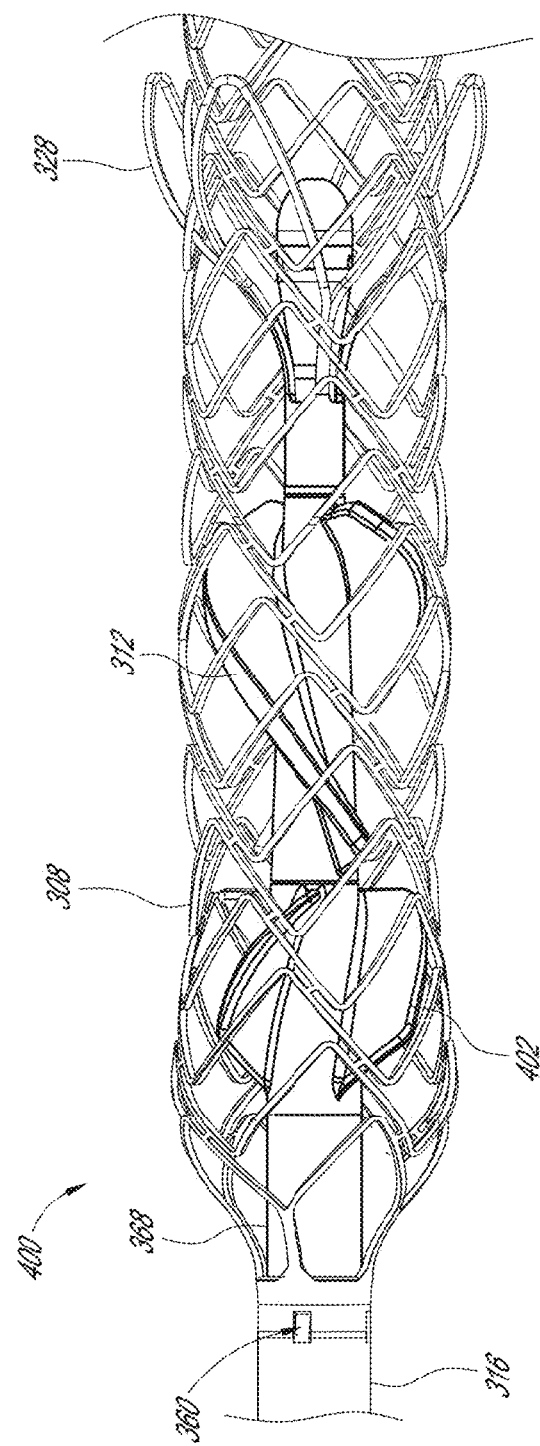
Figure 16:
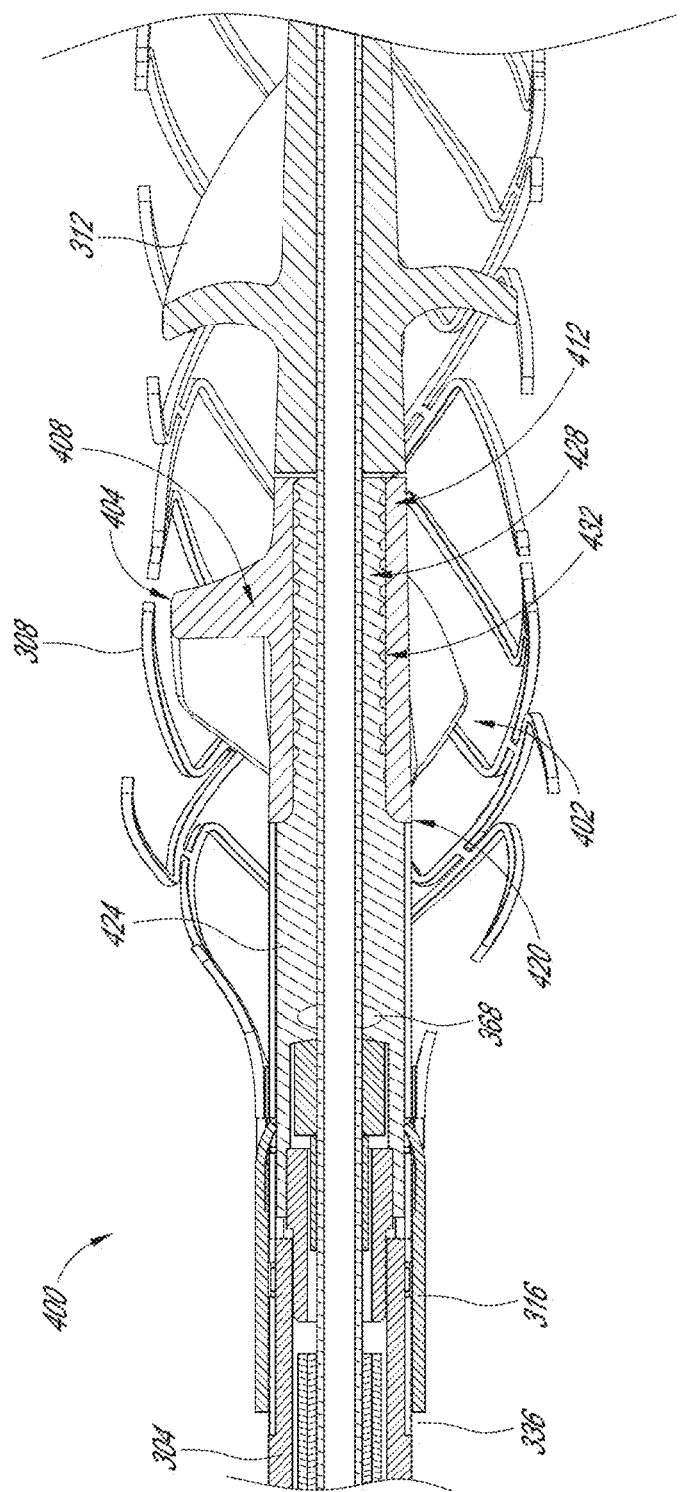

FIGS. 15-17 show details of a catheter assembly 400 having a stator assembly 402 disposed in a distal portion thereof. The stator assembly 402 enhances the performance of a catheter pump including the catheter assembly 400. The stator assembly 402 can include a stator blade body 404 having one or a plurality of, e.g., three, blades 408 extending outwardly from a central boy 412. The stator blade body 404 is at a downstream location of the impeller 312. In a percutaneous left ventricle application, the stator blade body 404 is disposed proximal of the impeller 312. In a percutaneous right ventricle application, the stator blade body 404 is located distal of the impeller 312. In a trans apical approach to aid the left ventricle, which might be provided through ports in the chest wall or via thoracotomy or mini-thoracotomy, the stator blade body 404 is disposed distal of the impeller 312.

The stator blades 408 are configured to act on the fluid flow generated by the impeller 312 to provide a more optimal fluid flow regime downstream of the stator assembly 402. This fluid flow regime can correspond to a more optimal fluid flow regime out of the outlet of the catheter pump. The stator blades 408 preferably convert at least the radial component of flow generated by the impeller 312 to a flow that is substantially entirely axial. In some cases, the stator blades 408 are configured to reduce other inefficiencies of the flow generated by the impeller 312, e.g., minimize turbulent flow, flow eddies, etc. Removing the radial components of the flow can be achieved with blades that are oriented in an opposite direction to the orientation of the blades of the impeller 312, for example, clockwise versus counterclockwise oriented blade surface.

While the stator blades 408 act on the flow generated by the impeller 312, the fluids also act on the stator assembly 402. For example, the stator blade body 404 experiences a torque generated by the interaction of the blades 408 with the blood as it flows past the stator assembly 402. A robust mechanical interface 420 is provided between the central body 412 and a distal portion of the catheter assembly 400. A bearing housing 424 is provided that is similar to the bearing housing 372, except as described differently below. The bearing housing 424 includes an elongate portion 428 that projects into a lumen of the central body 412. The elongate portion 428 preferably has an outer periphery that is smaller than an outer periphery of a portion of the bearing housing 424 immediately proximal of the elongate portion 428.

This structure provides an interface 432 disposed between the elongate portion and the portion just distal thereto. The interface 432 can be a shoulder having a radial extent that is approximately equal to that of the central body 412. In some embodiments, a flush surface is provided between the outer surface of the central body 412 and a distal outer surface of the sleeve 368 such that the radial extent of the shoulder of the interface 432 is less than that of the central body 412 by an amount approximately equal to the thickness of the sleeve 368. The interface 432 can also or alternately includes an engagement feature between the inner surface of the lumen of the central body 412 and the outer surface of the elongate portion 428. In one embodiment, the outer surface of the elongate portion 428 has a helical projection or groove and the central body 412 has corresponding and mating helical grooves or projections. These features can be or can be analogous to screw threads. Preferably the helix portion is arranged such that the torque felt by the stator assembly 402 generates a tightening of the engagement between the elongate portion 428 and the central body 412. The projections or grooves in the central body 412 can be formed by molding the central body 412 over the elongate projection 428.

A small gap is provided between the stator assembly 402 and the impeller 312 such that no or minimal contact is provided between these components, but the flow between the blades of these structures smoothly transitions between the blades thereof. Such an arrangement is useful in that the impeller 312 rotates at more than 10,000 RPM while the stator assembly 412 is stationary.

While the robust mechanical interfaces between the catheter body 104 and the cannula 108 is important to the catheter assembly 300 the interface is even more important in certain embodiments of the catheter body 400 that are actuated to a collapsed state prior to being removed from the patient. In such embodiments, the deployed working end preferably is collapsed, including the cannula 308, the stator blade body 404, and the impeller 312. This can be done by providing distal relative motion of the sheath assembly 88. The forces applied by the sheath assembly 88 to the catheter body 400, stator blade body 404, and the impeller 312 and focused at the mechanical joints are enhanced due to the presence of the stator blade body 404.

One will appreciate from the description herein that the catheter assembly may be modified based on the respective anatomy to suit the desired vascular approach. For example, the catheter assembly in the insertion state may be shaped for introduction through the subclavian artery to the heart. The catheter pump may be configured for insertion through a smaller opening and with a lower average flow rate for right side support. In various embodiments, the catheter assembly is scaled up for a higher flow rate for sicker patients and/or larger patients.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter pump, comprising:
   a catheter body having at least one lumen therethrough, and comprising a distal end and a proximal end;
   an expandable impeller assembly, the expandable impeller assembly including an expandable impeller and an expandable cannula coupled to the distal end of the catheter body and housing the expandable impeller, the expandable cannula comprising a substantially straight segment having a distal inlet and a proximal outlet;
   wherein the catheter body comprises a proximal vessel contact zone and a distal vessel contact zone that are each proximal to the substantially straight segment, the proximal vessel contact zone and distal vessel contact zone having a stiffness configured to, when formed in a curved shape deployed around an outer radius of the aortic arch, bear against the outer radius of the aortic arch with a restoring force in order to retain the catheter body in place around the outer radius of the aortic arch, thereby stabilizing the substantially straight segment when straddled across an aortic valve.

2. The catheter pump according to claim 1, further comprising a sheath assembly disposed over the catheter body, the sheath assembly configured to bear against at least one of the proximal vessel contact zone and the distal vessel contact zone.

3. The catheter pump according to claim 2, wherein the sheath assembly comprises a variable stiffness along a length thereof.

4. The catheter pump according to claim 2, wherein the sheath assembly is configured to translate longitudinally with respect to the expandable impeller assembly.

5. The catheter pump according to claim 4, wherein the sheath assembly comprises a distal tip configured to contact the expandable cannula to facilitate collapsing the expandable impeller assembly.

6. The catheter pump according to claim 5, wherein the distal tip of the sheath assembly comprises a flexible material.

7. The catheter pump according to claim 6, wherein the flexible material comprises an elastic polymer.

8. The catheter pump according to claim 2, wherein the sheath assembly comprises an inner liner portion and an outer jacket portion, the inner liner portion having a lower coefficient of friction than the outer jacket portion.

9. The catheter pump according to claim 1, wherein the expandable cannula comprises a non-expandable tubular portion proximal to an expandable portion of the expandable cannula, the non-expandable tubular portion anchoring the expandable cannula to the catheter body.

10. The catheter pump according to claim 1, wherein a highest stiffness portion of the catheter body is located at the distal end of the catheter body coupled to the expandable cannula.

11. The catheter pump according to claim 1, wherein the at least one lumen is configured to house a rotatable drive shaft therein.

12. The catheter pump according to claim 1, wherein the catheter body has a material hardness of less than 100 D and a flexural modulus of less than 400 MPa.

13. The catheter pump according to claim 1, further comprising a sheath assembly disposed over the catheter body, the sheath assembly comprising a proximal portion having a first hardness, and a middle portion located distal of the proximal portion and having a second hardness that is lower than the first hardness.

14. The catheter pump according to claim 13, wherein the sheath assembly further comprises a distal portion having a third hardness located distal of the middle portion, the third hardness being lower than the first hardness and also lower than the second hardness.

15. The catheter pump according to claim 13, wherein the middle portion is configured to cover the expandable impeller assembly when the impeller assembly is in a collapsed configuration.

16. The catheter pump according to claim 13, wherein the sheath assembly has a wall thickness of from 0.001 inch to 0.005 inch.

17. The catheter pump according to claim 13, wherein an inner diameter of the sheath assembly is from 0.1 inch to 0.2 inch.

18. The catheter pump according to claim 13, wherein the sheath assembly comprises a braided structure along at least a portion of the sheath assembly that increases the strength of the sheath assembly.

19. The catheter pump according to claim 13, wherein the sheath assembly comprises one or more position markers configured to indicate a position or orientation of the catheter pump within a human body.

20. The catheter pump according to claim 1, wherein the expandable cannula comprises a polymeric film covering at least the substantially straight segment.

* * * * *